(12) United States Patent
Scheltienne et al.

(10) Patent No.: US 11,471,682 B2
(45) Date of Patent: Oct. 18, 2022

(54) METHOD AND SYSTEM FOR PROVIDING MULTI-CHANNEL AND/OR NEUROSTIMULATION

(71) Applicant: ONWARD MEDICAL N.V., Eindhoven (NL)

(72) Inventors: Mathieu Scheltienne, Eindhoven (NL); Jeroen Tol, Eindhoven (NL); Edoardo Paoles, Eindhoven (NL); Jurriaan Bakker, Eindhoven (NL)

(73) Assignee: ONWARD MEDICAL N.V., Eindhoven (NL)

( * ) Notice: Subject to any disclaimer, the term of this patent is extended or adjusted under 35 U.S.C. 154(b) by 0 days.

(21) Appl. No.: 15/931,471

(22) Filed: May 13, 2020

(65) Prior Publication Data

US 2020/0360693 A1 Nov. 19, 2020

(30) Foreign Application Priority Data

May 13, 2019 (EP) .................................... 19174017

(51) Int. Cl.
*A61N 1/36* (2006.01)
*A61N 1/32* (2006.01)
*A61N 1/372* (2006.01)

(52) U.S. Cl.
CPC ......... *A61N 1/36071* (2013.01); *A61N 1/323* (2013.01); *A61N 1/36062* (2017.08); *A61N 1/37247* (2013.01)

(58) Field of Classification Search
CPC ............ A61N 1/36071; A61N 1/36062; A61N 1/323; A61N 1/37247
See application file for complete search history.

(56) References Cited

U.S. PATENT DOCUMENTS

| 4,398,537 A | 8/1983 | Holmbo |
| 8,543,200 B2 | 9/2013 | Lane et al. |
| 8,768,481 B2 | 7/2014 | Lane |

(Continued)

FOREIGN PATENT DOCUMENTS

| WO | 2014005075 A1 | 1/2014 |
| WO | 2014149895 A1 | 9/2014 |

OTHER PUBLICATIONS

Courtine, G. et al., "Transformation of nonfunctional spinal circuits into functional states after the loss of brain input," Nature Neuroscience, vol. 12, No. 10, Oct. 2009, Available Online Sep. 20, 2009, 20 pages.

(Continued)

*Primary Examiner* — Joseph M Dietrich
(74) *Attorney, Agent, or Firm* — Finnegan, Henderson, Farabow, Garrett & Dunner, LLP

(57) ABSTRACT

Methods and systems for neurostimulation are provided. In one example, a neurostimulation system may include a stimulation module, the stimulation module providing a first stimulation block and a second stimulation block. The neurostimulation system may further include a stimulation interference estimation module for providing an interference model for estimating a spatial interference between the first stimulation block and the second stimulation block. In some examples, the stimulation interference estimation module may reconfigure one or more of the first and the second stimulation blocks to reduce temporal overlap of the stimulation blocks.

22 Claims, 16 Drawing Sheets

(56) References Cited

U.S. PATENT DOCUMENTS

| | | |
|---|---|---|
| 2003/1200323 | 10/2003 | Dold et al. |
| 2011/0054568 A1 | 3/2011 | Lane et al. |
| 2011/0054570 A1 | 3/2011 | Lane |
| 2011/0160810 A1 | 6/2011 | Griffith |
| 2012/0116476 A1 | 5/2012 | Kothandaraman |
| 2014/0005753 A1 | 1/2014 | Carbunaru |
| 2014/0074190 A1 | 3/2014 | Griffith |
| 2015/0328462 A1 | 11/2015 | Griffith |
| 2018/0110992 A1* | 4/2018 | Parramon .......... A61N 1/37247 |

OTHER PUBLICATIONS

Dominici, N. et al., "Versatile robotic interface to evaluate, enable and train locomotion and balance after neuromotor disorders," Nature Medicine, vol. 18, No. 7, Jul. 2012, Published Online May 31, 2012, 8 pages.

Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.

Wenger, N. et al., "Closed-loop neuromodulation of spinal sensorimotor circuits controls refined locomotion after complete spinal cord injury," Science Translational Medicine, vol. 6, No. 255, Sep. 24, 2014, 12 pages.

Wenger, N. et al., "Spatiotemporal neuromodulation therapies engaging muscle synergies improve motor control after spinal cord injury," Natural Medicine, vol. 22, No. 2, Feb. 2016, Available Online Jan. 18, 2016, 33 pages.

* cited by examiner

| | E1 | E2 | E3 | E4 | E7 | E8 | E9 | E10 | E11 | E12 | E13 | E14 | E5 | E6 | E16 | E15 |
|---|---|---|---|---|---|---|---|---|---|---|---|---|---|---|---|---|
| E15 | -1.0 | -1.0 | -1.0 | -1.0 | -0.5 | -0.5 | -0.5 | -0.5 | 0.0 | 0.0 | 0.0 | 0.0 | -1.0 | -0.7 | -0.3 | 0.0 |
| E16 | -0.7 | -0.7 | -0.7 | -0.7 | -0.2 | -0.2 | -0.2 | -0.2 | 0.3 | 0.3 | 0.3 | 0.3 | -0.7 | -0.3 | 0.0 | 0.3 |
| E6 | -0.3 | -0.3 | -0.3 | -0.3 | 0.2 | 0.2 | 0.2 | 0.2 | 0.7 | 0.7 | 0.7 | 0.7 | -0.3 | 0.0 | 0.3 | 0.7 |
| E5 | 0.0 | 0.0 | 0.0 | 0.0 | 0.5 | 0.5 | 0.5 | 0.5 | 1.0 | 1.0 | 1.0 | 1.0 | 0.0 | 0.3 | 0.7 | 1.0 |
| E14 | -1.0 | -1.0 | -1.0 | -1.0 | -0.5 | -0.5 | -0.5 | -0.5 | 0.0 | 0.0 | 0.0 | 0.0 | -1.0 | -0.7 | -0.3 | 0.0 |
| E13 | -1.0 | -1.0 | -1.0 | -1.0 | -0.5 | -0.5 | -0.5 | -0.5 | 0.0 | 0.0 | 0.0 | 0.0 | -1.0 | -0.7 | -0.3 | 0.0 |
| E12 | -1.0 | -1.0 | -1.0 | -1.0 | -0.5 | -0.5 | -0.5 | -0.5 | 0.0 | 0.0 | 0.0 | 0.0 | -1.0 | -0.7 | -0.3 | 0.0 |
| E11 | -1.0 | -1.0 | -1.0 | -1.0 | -0.5 | -0.5 | -0.5 | -0.5 | 0.0 | 0.0 | 0.0 | 0.0 | -1.0 | -0.7 | -0.3 | 0.0 |
| E10 | -0.5 | -0.5 | -0.5 | -0.5 | 0.0 | 0.0 | 0.0 | 0.0 | 0.5 | 0.5 | 0.5 | 0.5 | -0.5 | -0.2 | 0.2 | 0.5 |
| E9 | -0.5 | -0.5 | -0.5 | -0.5 | 0.0 | 0.0 | 0.0 | 0.0 | 0.5 | 0.5 | 0.5 | 0.5 | -0.5 | -0.2 | -0.2 | 0.5 |
| E8 | -0.5 | -0.5 | -0.5 | -0.5 | 0.0 | 0.0 | 0.0 | 0.0 | 0.5 | 0.5 | 0.5 | 0.5 | -0.5 | -0.2 | 0.2 | 0.5 |
| E7 | -0.5 | -0.5 | -0.5 | -0.5 | 0.0 | 0.0 | 0.0 | 0.0 | 0.5 | 0.5 | 0.5 | 0.5 | -0.5 | -0.2 | 0.2 | 0.5 |
| E4 | 0.0 | 0.0 | 0.0 | 0.0 | 0.5 | 0.5 | 0.5 | 0.5 | 1.0 | 1.0 | 1.0 | 1.0 | 0.0 | 0.3 | 0.7 | 1.0 |
| E3 | 0.0 | 0.0 | 0.0 | 0.0 | 0.5 | 0.5 | 0.5 | 0.5 | 1.0 | 1.0 | 1.0 | 1.0 | 0.0 | 0.3 | 0.7 | 1.0 |
| E2 | 0.0 | 0.0 | 0.0 | 0.0 | 0.5 | 0.5 | 0.5 | 0.5 | 1.0 | 1.0 | 1.0 | 1.0 | 0.0 | 0.3 | 0.7 | 1.0 |
| E1 | 0.0 | 0.0 | 0.0 | 0.0 | 0.5 | 0.5 | 0.5 | 0.5 | 1.0 | 1.0 | 1.0 | 1.0 | 0.0 | 0.3 | 0.7 | 1.0 |

Fig. 5

|    | E1 | E2 | E3 | E4 | E7 | E8 | E9 | E10 | E11 | E12 | E13 | E14 | E5 | E6 | E16 | E15 |
|----|----|----|----|----|----|----|----|-----|-----|-----|-----|-----|----|----|-----|-----|
| E1 | 0.0 | 1.0 | 2.0 | 3.0 | -0.5 | 0.5 | 1.5 | 2.5 | 0.0 | 1.0 | 2.0 | 3.0 | 4.0 | 4.0 | 4.0 | 4.0 |
| E2 | -1.0 | 0.0 | 1.0 | 2.0 | -1.5 | -0.5 | 0.5 | 1.5 | -1.0 | 0.0 | 1.0 | 2.0 | 3.0 | 3.0 | 3.0 | 3.0 |
| E3 | -2.0 | -1.0 | 0.0 | 1.0 | -2.5 | -1.5 | -0.5 | 0.5 | -2.0 | -1.0 | 0.0 | 1.0 | 2.0 | 2.0 | 2.0 | 2.0 |
| E4 | -3.0 | -2.0 | -1.0 | 0.0 | -3.5 | -2.5 | -1.5 | -0.5 | -3.0 | -2.0 | -1.0 | 0.0 | 1.0 | 1.0 | 1.0 | 1.0 |
| E7 | 0.5 | 1.5 | 2.5 | 3.5 | 0.0 | 1.0 | 2.0 | 3.0 | 0.5 | 1.5 | 2.5 | 3.5 | 4.5 | 4.5 | 4.5 | 4.5 |
| E8 | -0.5 | 0.5 | 1.5 | 2.5 | -1.0 | 0.0 | 1.0 | 2.0 | -0.5 | 0.5 | 1.5 | 2.5 | 3.5 | 3.5 | 3.5 | 3.5 |
| E9 | -1.5 | -0.5 | 0.5 | 1.5 | -2.0 | -1.0 | 0.0 | 1.0 | -1.5 | -0.5 | 0.5 | 1.5 | 2.5 | 2.5 | 2.5 | 2.5 |
| E10 | -2.5 | -1.5 | -0.5 | 0.5 | -3.0 | -2.0 | -1.0 | 0.0 | -2.5 | -1.5 | -0.5 | 0.5 | 1.5 | 1.5 | 1.5 | 1.5 |
| E11 | 0.0 | 1.0 | 2.0 | 3.0 | -0.5 | 0.5 | 1.5 | 2.5 | 0.0 | 1.0 | 2.0 | 3.0 | 4.0 | 4.0 | 4.0 | 4.0 |
| E12 | -1.0 | 0.0 | 1.0 | 2.0 | -1.5 | -0.5 | 0.5 | 1.5 | -1.0 | 0.0 | 1.0 | 2.0 | 3.0 | 3.0 | 3.0 | 3.0 |
| E13 | -2.0 | -1.0 | 0.0 | 1.0 | -2.5 | -1.5 | -0.5 | 0.5 | -2.0 | -1.0 | 0.0 | 1.0 | 2.0 | 2.0 | 2.0 | 2.0 |
| E14 | -3.0 | -2.0 | -1.0 | 0.0 | -3.5 | -2.5 | -1.5 | -0.5 | -3.0 | -2.0 | -1.0 | 0.0 | 1.0 | 1.0 | 1.0 | 1.0 |
| E5 | -4.0 | -3.0 | -2.0 | -1.0 | -4.5 | -3.5 | -2.5 | -1.5 | -4.0 | -3.0 | -2.0 | -1.0 | 0.0 | 0.0 | 0.0 | 0.0 |
| E6 | -4.0 | -3.0 | -2.0 | -1.0 | -4.5 | -3.5 | -2.5 | -1.5 | -4.0 | -3.0 | -2.0 | -1.0 | 0.0 | 0.0 | 0.0 | 0.0 |
| E16 | -4.0 | -3.0 | -2.0 | -1.0 | -4.5 | -3.5 | -2.5 | -1.5 | -4.0 | -3.0 | -2.0 | -1.0 | 0.0 | 0.0 | 0.0 | 0.0 |
| E15 | -4.0 | -3.0 | -2.0 | -1.0 | -4.5 | -3.5 | -2.5 | -1.5 | -4.0 | -3.0 | -2.0 | -1.0 | 0.0 | 0.0 | 0.0 | 0.0 |

Fig. 6

| COMBINATION | $D_X$ | $D_Y$ |
|---|---|---|
| E7 / E11 | 0.5 | 0.5 |
| E7 / E4 | 0.5 | 3.5 |
| E7 / E14 | 0.5 | 3.5 |
| E7 / E6 | 0.17 | 4.5 |
| E11 / E4 | 1 | 3 |
| E11 / E14 | 0 | 3 |
| E11 / E6 | 0.66 | 4 |
| E4 / E14 | 1 | 0 |
| E4 / E6 | 0.33 | 1 |
| E6 / E14 | 0.66 | 1 |

Fig. 7

|    | E1    | E2    | E3    | E4    | E5    | E6    | E7    | E8    | E9    | E10   | E11   | E12   | E13   | E14   | E15   | E16   |
|----|-------|-------|-------|-------|-------|-------|-------|-------|-------|-------|-------|-------|-------|-------|-------|-------|
| E1 | 712.6 | 30.1  | 16.6  | 10.0  | 6.2   | 6.0   | 40.4  | 41.3  | 21.1  | 12.3  | 42.8  | 28.5  | 16.4  | 9.9   | 6.2   | 6.1   |
| E2 | 30.1  | 719.7 | 30.7  | 16.9  | 10.4  | 10.1  | 21.2  | 43.1  | 44.3  | 21.3  | 28.5  | 46.2  | 28.9  | 16.7  | 10.4  | 10.2  |
| E3 | 16.6  | 30.7  | 715.7 | 29.7  | 17.0  | 16.5  | 12.4  | 21.0  | 43.7  | 41.8  | 16.4  | 28.9  | 45.1  | 28.2  | 16.8  | 16.5  |
| E4 | 10.0  | 16.9  | 29.7  | 708.2 | 28.9  | 27.9  | 7.5   | 12.3  | 21.3  | 40.2  | 9.9   | 16.7  | 28.2  | 42.1  | 27.5  | 27.6  |
| E5 | 6.2   | 10.4  | 17.0  | 28.9  | 708.7 | 63.0  | 4.7   | 7.7   | 12.9  | 20.7  | 6.2   | 10.4  | 16.8  | 27.5  | 41.3  | 47.4  |
| E6 | 6.2   | 10.5  | 17.0  | 28.9  | 65.1  | 713.0 | 4.7   | 7.7   | 13.0  | 20.9  | 6.2   | 10.4  | 16.9  | 28.3  | 48.3  | 65.0  |
| E7 | 42.4  | 22.2  | 13.0  | 7.9   | 4.9   | 4.8   | 753.7 | 28.9  | 16.4  | 9.7   | 42.1  | 22.1  | 12.9  | 7.9   | 4.9   | 4.8   |
| E8 | 43.4  | 45.2  | 22.0  | 13.0  | 8.1   | 7.8   | 28.9  | 756.5 | 30.0  | 16.1  | 43.0  | 44.9  | 21.9  | 12.9  | 8.0   | 7.9   |
| E9 | 22.2  | 46.5  | 45.8  | 22.4  | 13.6  | 13.2  | 16.4  | 30.0  | 762.1 | 30.0  | 22.1  | 46.1  | 45.5  | 22.3  | 13.5  | 13.2  |
| E10| 12.9  | 22.3  | 43.9  | 42.3  | 21.8  | 21.3  | 9.7   | 16.1  | 30.0  | 753.7 | 12.8  | 22.2  | 43.6  | 41.9  | 21.7  | 21.3  |
| E11| 43.0  | 28.6  | 16.5  | 10.0  | 6.2   | 6.0   | 40.2  | 41.1  | 21.1  | 12.3  | 742.5 | 29.9  | 16.5  | 9.9   | 6.2   | 6.1   |
| E12| 28.6  | 46.4  | 29.0  | 16.8  | 10.4  | 10.1  | 21.2  | 43.0  | 44.1  | 21.3  | 30.0  | 749.5 | 30.5  | 16.8  | 10.4  | 10.2  |
| E13| 16.5  | 29.0  | 45.3  | 28.3  | 16.9  | 16.5  | 12.4  | 21.0  | 43.5  | 41.7  | 16.5  | 30.5  | 745.6 | 29.6  | 16.9  | 16.6  |
| E14| 9.9   | 16.8  | 28.3  | 42.3  | 27.6  | 27.5  | 7.5   | 12.3  | 21.3  | 40.0  | 9.9   | 16.8  | 29.5  | 737.9 | 28.7  | 28.0  |
| E15| 6.2   | 10.4  | 16.9  | 27.6  | 41.5  | 47.0  | 4.7   | 7.7   | 12.9  | 20.7  | 6.2   | 10.4  | 16.9  | 28.8  | 738.6 | 63.4  |
| E16| 6.2   | 10.4  | 17.0  | 28.4  | 48.8  | 64.8  | 4.7   | 7.7   | 13.0  | 20.9  | 6.2   | 10.4  | 17.0  | 28.8  | 65.0  | 750.9 |

Fig. 8

| COMBINATION | R-VALUE [Ohm] |
|---|---|
| E7 / E11 | 42.1 |
| E7 / E4 | 7.9 |
| E7 / E14 | 7.9 |
| E7 / E6 | 4.8 |
| E11 / E4 | 9.9 |
| E11 / E14 | 9.9 |
| E11 / E6 | 6.2 |
| E4 / E14 | 42.1 |
| E4 / E6 | 27.9 |
| E6 / E14 | 28.3 |

Fig. 9

METHOD AND SYSTEM FOR PROVIDING MULTI-CHANNEL AND/OR NEUROSTIMULATION

CROSS-REFERENCE TO RELATED APPLICATION

The present application claims priority to European Patent Application No. 19174017.4 filed on May 13, 2019. The entire contents of the above-listed application is hereby incorporated by reference for all purposes.

TECHNICAL FIELD

The present disclosure relates to a method and system for providing multi-channel variable neuromodulation.

BACKGROUND AND SUMMARY

Epidural electrostimulation (EES) shows promising results for spinal cord injury therapy. The mechanisms are still unclear and under investigation, but EES can both stimulate the leg muscles through the proprioceptive afferent fibers and restore the neuronal network in the spinal cord. EES uses a multi-electrode array placed on the dorsal side of the spinal cord on top of the dura matter. In rats, the combination of serotonergic agonists and EES was able to acutely transform spinal networks from non-functional to highly functional and adaptive states as early as one week after injury (Courtine G, et al., *Transformation of nonfunctional spinal circuits into functional states after the loss of brain input. Nature neuroscience* 12, 1333-1342, (2009)). Moreover, EES also restores voluntary control of locomotion by rewiring the injured spinal cord area (Wenger N et al., *Spatiotemporal neuromodulation therapies engaging muscle synergies improve motor control after spinal cord injury, Nature Medicine* 22, 138-145 (2016)). However, EES alone is not sufficient. Combination with either drugs injection or robotic assisted therapy such as a bodyweight support system improves the recovery (Dominici N et al., *Versatile robotic interface to evaluate, enable and train locomotion and balance after neuromotor disorders, Nature medicine* 18, 1142-1147 (2012)).

Because of the complexity of the spinal cord, delivering EES stimulation on the multi-electrode array (lead) implanted is quite challenging. Computational models were designed and tested on both rats and human (Capogrosso M, et al., *A Computational Model for Epidural Electrical Stimulation of Spinal Sensorimotor Circuits, Journal of Neuroscience* 4 Dec. 2013, 33 (49) 19326-19340) to evaluate the neuronal and muscular response to the stimulation, as well as closed-loop neuromodulation systems that refined locomotion after complete spinal cord injury (Wenger N et al., *Closed-loop neuromodulation of spinal sensorimotor circuits controls refined locomotion after complete spinal cord injury, in Science Translational Medicine, vol. 6, num. 255*, 2014).

The degree of control required on the neurostimulation restricts largely the available stimulation settings (stimulus space). The stimulation settings must comply with hardware limitations, with requirements on the predictive capability of the system and with safety regulatory norms. For instance, the hardware has a limited power supply, the stimulation outcome (muscle activation) must be controlled, and the electrode chemical stability must be insured independently of the stimulation settings used.

Each muscle has a different response according to the nerve fibers stimulation settings. Each muscle is associated with nerve fibers and a stimulation area on the implanted lead. The muscle response will vary with the amplitude, but also with the frequency, the pulse shape, or the use of burst of pulses rather than continuous frequency stimulation.

A stimulation block (SB) determines (an) electrode configuration, (an) amplitude/intensity of stimulation and a pulse train, wherein a pulse train may be defined as a temporal arrangement of stimulation events. Thus, during movement, e.g. a gait cycle, different stimulation blocks need to be stimulated simultaneously with different pulsed electrical waveforms at different frequencies and amplitudes, sometimes with different pattern of pulses, in order to reproduce a movement, e.g. cycle comparable to a healthy subject.

Multiple channel (i.e. multiple stimulation blocks, pulsed electrical waveforms) variable frequency neurostimulation is harder to control since the neurostimulation's pulses might temporally and/or spatially overlap. Overlapping of pulses creates several issues. It is hardly possible to output two pulses on the same electrode simultaneously; and if the electrodes are different, the overlapping of two pulses will require a higher voltage on the power supply line, and thus will draw out more power from the battery than if they were outputted one after the other. This second point is critical in implantable devices since the battery life time is one of the main concerns. The muscle response (outcome) achieved with temporally overlapping pulses will potentially differ from the outcome reached with the same pulses taken separately. Current knowledge of the muscle response induced by spinal cord neurostimulation is limited to strictly orthogonal pulsing.

Thus, to stimulate in a controlled fashion and in a secure way, while drawing as little power as possible from the battery, a solution to avoid spatial and/or temporal overlap of the pulse trains of different stimulation blocks is needed.

One method to avoid a temporal overlap of the pulses between pulsed electrical waveforms is to allow only one pulse at a time, and to delay the others. The method, called the "token approach", is described in the patent "US20110054568A1" assigned to the "Boston Scientific Neuromodulation Corporation". If two pulse generators want to output a pulse at the same time, one gets the priority and the other is delayed. Other patents on close-by methods identified as pulse positioning methods were also filed by the same company ("U.S. Pat. No. 8,543,200B2", "U.S. Pat. No. 8,768,481B2"). They aim to place the pulses on the timeline in such a way that pulses don't bump into each other, in other words, that temporal overlap is avoided. With these methods, each pulsed electrical waveform will not have a constant frequency, but an instantaneous frequency within a jitter specification. For instance, the requirement can bound the jitter at 10% of the nominal frequency for each pulsed electrical waveform. Thus, at any given instant, a pulsed electrical waveform at the nominal frequency 40 Hz will have its instantaneous frequency between 36 Hz and 44 Hz.

US 2003/1200323 A1 relates to a re-chargeable spinal cord stimulator system, which includes multiple electrodes, multiple, independently programmable, stimulation channel with an implantable pulse generator, which channels can provide concurrent, but unique stimulation fields, permitting virtual electrodes to be realized.

U.S. Pat. No. 4,398,537 relates to an independently rate-adjusting multiple channel controller for nerve stimulator transmitter to be used in conjunction with implanted stimulation pulse output unit, wherein an event that two or more trigger signals coincide in the transmitting circuit, the rate control circuit blocks and delays the latter occurring trigger signal with only minor or insignificant effect on a trigger signal rate.

WO 2014/005075 A1 and US 2014/0005753 A1 relates to a system compounding low-frequency sources for high-frequency neuromodulation, where the system has a control circuitry configured for operating the switching network to concurrently convey the plurality of electrical pulse trains for a plurality of electrical terminals to a common electrical terminal, thereby creating a combined electrical pulse train having an average pulse rate equal to or greater than 1 KHz.

US 2011/0160810 A1 relates to a multi-channel neurostimulation system comprising a plurality of electrical terminals configured for being respectively coupled to a plurality of electrodes, stimulation output circuitry including electrical source circuitry of the same polarity configured for generating a polarity of pulse electrical waveforms in a plurality of timing channels. Furthermore, there is a control circuitry configured for instructing the stimulation output circuitry to serially couple the electrical source circuitry to different sets of the electrodes when pulses of the respective pulsed electrical waveforms do not temporarily overlap each other, and for instructing the stimulation output circuitry to couple the electrical source circuitry to a union of the different electrode sets when pulses of the respective pulsed electrical waveforms temporarily overlap each other.

US 2012/0116476 A1 relates to a system and method for storing application specific and lead configuration information in a neurostimulation device, whereas the control device is able to re-program the neurostimulator.

US 2015/0328462 relates to a system and method for independently operating multiple neurostimulation channels. The system comprises a control circuitry configured for instructing the stimulation output circuitry to serially couple the electrical source circuitry to different sets of electrodes when pulses of the respective pulse electrical waveforms do not temporarily overlap each other and for instructing the stimulation output circuitry to couple the electrical source circuitry to a union of the different electrode sets when pulses of the respective pulsed electrical way forms temporarily overlap each other.

WO 2014/149895 A1 relates to a neuromodulation system method thereto. Here, a first electrical modulation energy to a patient is delivered through a timing channel at the relatively high energy level during a first time period in accordance with a stored modulation energy delivery schedule, and a second electrical modulation energy is delivered to the patient through the same timing channel at the relatively low energy level during a second level time period in accordance with the stored modulation energy delivery schedule.

Furthermore, US 2014/0074190 relates to a multi-channel neurostimulation system comprising a plurality of electrical terminals configured for being respectively coupled to a plurality of electrodes. Moreover, there is a stimulation output circuitry including electrical source circuitry of the same polarity configured for generating a plurality of pulsed electrical waveforms in a plurality of timing channels, and control circuitry configured for instructing the stimulation output circuitry to serially couple the electrical source circuitry to different sets of the electrodes when pulses of the respective pulsed electrical waveforms do not temporally overlap each other, and for instructing the stimulation output circuitry to couple the electrical source circuitry to a union of the different electrode sets when pulses of the respective pulsed electrical waveforms temporarily overlap each other.

US 2011/0054570 relates to a method and external control device for preventing frequency locking in a multi-channel neurostimulation system and external control device. A plurality of pulse electrical waveforms is provided. Each of the pulse electrical waveforms has a period and a pulse width. The greatest common divisor of the periods of the pulse electrical waveform is computed, and the sum of the pulse widths of the pulse electrical waveforms is computed. A plurality of timing channels and the neurostimulation is allowed to be programmed with the pulsed electrical waveforms if the greatest common divisor is equal to or greater than the sum.

It is therefore an object of the present invention to provide a solution for a system and method that can better manage partial and full overlap of multichannel and/or variable neuromodulation/neurostimulation, also using a plurality of waveforms, and to enhance multi-channel and/or variable neurostimulation.

This object is solved by the system according to claim 1. Accordingly, a system for a multi-channel and/or variable neurostimulation, at least comprising: at least one stimulation module for providing a. at least a first stimulation block, the first stimulation block comprising a first electrode configuration, a first amplitude, and a pulse train, especially wherein the first pulse train comprises a first temporal arrangement of stimulation events; and b. at least a second stimulation block, the second stimulation block comprising a second electrode configuration, a second amplitude, and a second pulse train, especially wherein the second pulse train comprises a second temporal arrangement of stimulation events;

c. at least one stimulation interference estimation module for providing an interference model for estimating the first stimulation block and the second stimulation block for at least one potential spatial and/or temporal overlap, wherein the stimulation interference estimation module is configured and arranged such that in case of an estimated spatial and/or temporal overlap of stimulation blocks, the first stimulation block and/or the second stimulation block are reconfigured as to avoid at least partially the spatial and/or temporal overlap of stimulation blocks.

Of note, there can be two stimulation blocks or three or even more stimulation blocks.

The invention is based on the basic idea that temporal overlapping of stimulation events of pulse trains of different stimulation blocks, which can happen in multi-channel and/or variable frequency neurostimulation, has to be avoided or minimized to limit the potential, adverse impact on the intended therapy.

Ordinary multi-channel and/or variable neurostimulation may lead to overlapping of pulse trains of different stimulation blocks, which is unwanted as such overlapping may lead to unwanted effects. Such effects may happen in various ranges and may be tolerable to some extent, but for example when exceeding e.g. pre-determined criteria or pre-set boundaries, they may be intolerable and must be avoided. One important point is the finding of the inventors to detect stimulation interference if pulse overlap cannot be avoided. Interference between pulse trains of stimulation blocks which are active at the same time is estimated by an interference model and, on this basis, the provided multi-channel and/or variable neurostimulation is optimized so that this interference is minimized or eliminated. As a result, stimulation blocks whose electrode constellations, current levels and/or pulse trains lead to interference are identified.

Further, the current delivered to the electrode configuration of each stimulation block can be optimized or the electrode configuration of some or all stimulation blocks can be reconfigured if these stimulation blocks have overlapping pulses. Optimization can be done either offline and/or online and in real-time.

On the other hand, slight overlaps or overlaps, where the interference is low or which can be accepted as their impact has no or only effects, can be allowed and thus the operational range of the stimulation system is significantly broadened.

The system may secure the neurostimulation's outcome by determining which stimulation blocks are interfering based on the spatial distribution of the active electrodes, the considered pulse trains and current amplitude levels. Pulse trains reconfigured and forming different timing channels can no longer overlap fully or can only overlap partially and so stimulation effects that cause so called adverse side effects are prevented. Moreover, the system could also be used to optimize the current delivered by each stimulation block to trigger the desired action potential, and thus by extension of the energy consumption and the battery lifetime. Finally, to secure the neurostimulation's outcome, this invention may also involve online and/or offline electrode reconfiguration, for example, to overcome hardware limitations or reduce interference at the cost of specificity.

Thus, a better control of the neurostimulation can be provided with the system.

The term neurostimulation covers any type of neurostimulation, such as spinal cord neurostimulation, invasive and/or non-invasive stimulation (also covering combinations thereof), transcutaneous neurostimulation (tSCS), stimulation to enhance or restore autonomous functions of a patient, restoration and/or enhancement of movements of any body parts such as locomotion or movement of arms and hands of a patient, restoration and/or enhancement of blood pressure control, voluntary or any other control over muscles, pain treatment, deep brain stimulation, brain stimulation, any stimulation for the organs like heart stimulation, epidural stimulation (EES), functional electrical stimulation (FES), subdural stimulation, and the like.

The term pulse train as used in connection with the present disclosure is inter alia to be understood as a (neurostimulation) channel with one or more stimulation events such as at least one stimulation pulse occurring within the (chosen) finite period of time.

Alternative terms which are to be understood as being the same or covered by the term pulse train are pulse waveform and pulsed electrical waveform.

More specifically, a pulse train in the sense of this disclosure can be understood as a finite time period with one or more stimulation events comprising at least one stimulation pulse or stimulation burst. These events are occurring within the (chosen) finite period of time. A pulse train in this sense may have its own temporal arrangement such as a frequency or any aperiodic arrangement and may be provided on a (neurostimulation) channel. There can be two pulse trains or as shown in some examples, three or even more pulse trains.

There can be more than two stimulation blocks.

For a plurality of stimulation blocks delivering a plurality of multiphasic pulse electrical waveforms with equally or different pulse trains (e.g. frequencies), some of the pulses within the electrical waveforms may overlap partially of fully temporally with others.

The term temporal arrangement as used in the context of pulse trains in connection with the present disclosure is inter alia to be understood as covering any temporal arrangement of stimulation events such as periodic or aperiodic events. It also covers one or more frequencies of stimulation events or the like, but it is not limited to such events.

The term variable neurostimulation describes inter alia (but not limited only to this) that the provided neurostimulation can be varied especially in terms e.g. variation of stimulation blocks, e.g. of electrode configuration, amplitude, and/or a pulse train.

Generally speaking, the first stimulation block and the second stimulation block (and also any further stimulation block) may be realized in the same stimulation channel.

The system can be used for paddle and percutaneous leads, transcutaneous electrical nerve stimulation (TENS), and all neurostimulation and muscle stimulation applications comprising more than one electrode, and/or more than one lead.

In particular, the stimulation interference estimation module may be configured and arranged to analyze the spatial relationship of the first stimulation block and the second stimulation block.

In particular, the stimulation interference estimation module may estimate the interference between two or more stimulation blocks which are active at the same time. In particular, this estimation may be based on interference criteria which can either be a set of predefined rules or metrics computed to estimate the interference between stimulation blocks.

In particular, spatial sections may be determined. Determining spatial sections may be based on graph theory. Graph theory is used to model pairwise relations between objects. A graph is made of nodes connected by lines. Each segment of a stimulation partiture characterized by a fixed and unique set of stimulation blocks is associated with a graph in which the nodes are the stimulation blocks, and the lines are linking the interfering stimulation blocks. If a node is reachable from itself through a path of edges and nodes, then this path forms a cycle.

The grouping of the stimulation blocks into different spatial sections may be done according to the following methodological instructions:
 a. If two stimulation blocks providing pulse trains at the same time are interfering, they may be flagged as interfering,
 b. If two stimulation blocks providing pulse trains at the same time are not interfering, they may be flagged as not interfering,
 c. and then, the N-cycles in the resulting graph may be found. Each cycle may be a spatial section.

In particular, the stimulation interference estimation module may assess the spatial relationship of the first stimulation block and the second stimulation block that in case of a predetermined value indicating sufficient spatial distance between the first stimulation block and the second stimulation block complete temporal overlap of pulse trains is tolerated and in case of a predetermined value indicating insufficient spatial distance between the first stimulation block and the second stimulation block no temporal overlap of pulse trains is tolerated.

In other words, it is possible that the overlap of stimulation events of the first pulse train and the second pulse train is completely avoided with the system. This rule can be implemented and done semi-automatically or automatically. In other words, in the case of insufficient spatial distance between the first stimulation block and the second stimulation block, the system does not allow any overlap of pulses of the first stimulation block and the second stimulation block.

Alternatively, the stimulation interference estimation module may assess the spatial relationship of the first stimulation block and the second stimulation block, that in case of a predetermined degree of spatial interference between the first stimulation block and the second stimulation block, a predetermined degree of freedom is tolerated for a temporal overlap of pulse trains.

For instance, the three following levels of interference may be defined: interference, slight interference, no interference. Then different degrees of overlap may be allowed in the temporal domain:
  a. If two stimulation blocks do interfere no overlapping is allowed between the pulse trains of the two or more stimulation blocks;
  b. If two stimulation blocks do slightly interfere, overlapping of the cathodic phase (stimulation) with the anodic phase (post-stimulation) of pulses of the two or more stimulation blocks is allowed if the simulation blocks are not sharing electrodes; and
  c. If two stimulation blocks do not interfere overlapping of pulse trains is allowed.

From the interference procedure defined above, and depending on the model chosen, a more complex definition of the interference could be applied. A 2D matrix may be computed with each matrix value weighing the interference between the stimulation blocks. This may be extended to an N-dimensional matrix to cover combinations of stimulation blocks.

Moreover, this interference matrix may be customizable. For instance, a matrix computed from simulation may then be modified by the user if additional knowledge obtained through rehabilitation shows that assumed interfering stimulation blocks do not interact one with the other at an intolerable level. The other way around, two stimulation blocks which have a low interference weighting may be manually flagged as interfering by a user.

In other words, it is also possible that an overlap of the pulses is partly forbidden, which is less strict than a complete and strict avoidance of any overlap. For example, an overlap between stimulation pulses may be tolerated for a part of the pulses, e.g. 10% of the pulses of each waveform (or an individual percentage, e.g. 5% of the pulses from the first waveform, 12% of the pulses of the second waveform etc.).

Pulses may be composed of k phases, with k>1, wherein possible phases of pulses may include but are not limited to stimulation phase, pre-stimulation phase, post-stimulation phase and intra pulse delay phase (or Dip phase). It may be handled very strict, i.e. that the stimulation phase and also the pre-stimulation-phase and the post-stimulation phase may not overlap. In other words, there may be a definition that there is no overlap between a certain time frame, e.g. X microseconds or Y milliseconds after and before the pulse.

According to a possible embodiment, the pulse train and/or electrode configuration and/or stimulation currents of the first stimulation block and/or the second stimulation block may be reconfigured.

Predicting interference may also be used to optimize the injected current for the therapy. For instance, an activating function model, may be implemented, wherein a difference between a maximum value of the activating function and a threshold may determine an amount of injected current that is needed to reach the threshold and trigger an action potential, or that can be reduced to save battery lifetime without altering the therapeutic effect. This current optimization may be either performed in real-time or beforehand by a third-party method looking through the planned stimulation and optimizing the current for each pulse individually.

Additionally, and or alternatively, when interference is detected, the specific electrode configuration per stimulation block may be optimized to minimize the effect of interference while keeping the activation of the targeted fiber. For example, for interference involving two unipolar stimulation blocks, one of the stimulation blocks may have its electrode constellation changed to a multipolar setting shielding the cathode and preventing interference.

Electrode reconfiguration may also be considered to overcome hardware limitations.

For instance,
  a. if two stimulation blocks have their electrode configurations sharing an electrode, the stimulation hardware might not be able to generate the (superposition) pattern of currents if the two stimulation blocks have overlapping pulses;
  b. if pulses need to be output too close in time, the stimulation engine might not be able to change its output current amplitude fast enough to accommodate the newly required current.

An alternative suboptimal electrode configuration may be proposed for one or for both stimulation blocks so that the hardware is capable again to generate the desired stimulation pulses/patterns. The interference induced by the new electrode configurations may be reassessed and the spatial sections may be updated accordingly.

Another option to use electrode reconfiguration may be to minimize the impact of interference when overlap occurs. For example, at the cost of less specificity, if a suboptimal (from the perspective of selectivity) alternative electrode configuration or configurations are chosen that still perform better than the originally chosen electrode configurations during interference.

This optimization of the electrode configuration could be performed either beforehand or in real-time as the stimulation engine generates the desired waveforms.

The stimulation interference estimation module may be configured and arranged to calculate a spatial interference model of the first stimulation block and the second stimulation block on the basis of at least one of the options, such as distance rules, R-Matrix, generic neuronal model, activating function model or the like.

The interference between the stimulation blocks may depend on many parameters such as the distance between the involved electrodes. For a given lead, the relative electrode to electrode distance matrix along the X-axis and the Y-axis may be computed based on reference axes.

The stimulation blocks may be designated by their unipolar electrode configuration for readability purposes.

An R-Matrix may be used to predict the interference between the electrodes during e.g. unipolar stimulation. For instance, the R-Matrix may be computed for a multiple-electrodes lead using a 3D spinal cord model. An interference threshold might be defined.

The interference may also be defined at the level of the nerve fibers. Pulse overlapping might alter the expected firing rate of the targeted nerve fibers. Two overlapping stimulation blocks do not interfere if the firing rate of the targeted nerve fibers remains within a tolerance margin to the expected firing rate due to the stimulation blocks taken alone.

The interference may also be defined in terms of activating function. The activating function is proportional to a second derivative of the potential field along the nerve fiber and may be a very good indicator of the likelihood that nerve fibers will fire in response to the applied electric field. An action potential may be triggered where the activating function is above a certain threshold. This threshold may be unique for each fiber and may be estimated through neuronal simulations.

In particular, the spatial interference model may be a generic model or a patient specific model.

In other words, every model described above may be a generic model or made patient-specific if patient data are available.

In particular, the neuronal simulation may be performed with a patient-specific spinal cord model created from magnetic resonance imaging (MRI) data and/or computer tomography (CT) data or similar data to determine the anatomy of the spinal cord and the placement of the lead(s), respectively.

According to the present invention a method is disclosed, the method characterized in that the method is performed with the system as described above and/or hereinafter.

The system and method may be used in a close-loop fashion, taking into account exterior parameters to compute the interference matrix. For instance, a posture detection system could be coupled (either through inertia measurement units or e.g. impedance measurement or any other type of sensor) and used to compute an interference matrix in real-time to dynamically consider the effect of posture on the interference between the stimulation blocks.

However, the system and method may also be used in an open-loop fashion.

Also, it is possible the system is configured for open-loop and closed-loop. It is possible that the most suitable way can be chosen automatically and/or semi-automatically or on specific selection of the user.

The system for neurostimulation can be a transcutaneous system. It can be completely non-invasive.

Alternatively, the system for neurostimulation can be a system that is at least partially implantable or partially implanted (during treatment). Also, it can be embodied such that the system is completely/entirely implantable.

The system can comprise a stimulation interference estimation module.

The stimulation interference estimation module can be located in the implantable part of the neurostimulation system.

However, it is also possible that the stimulation interference estimation module is located in the non-implantable of the neurostimulation system.

The stimulation interference estimation module can be configured such that it computes the necessary adjustments in real-time and/or close to real-time.

In one example, the necessary adjustments may be pre-computed, and the pre-computed adjustment data may be stored in non-transitory memory of the stimulation interference estimation module.

BRIEF DESCRIPTION OF DRAWINGS

Further details and advantages of the present invention shall now be disclosed in connection with the drawings.

FIG. 5 shows a relative electrode to electrode distance matrix along the X-axis of a given lead, such as the lead shown in FIG. 4, according to an embodiment of the present invention;

FIG. 6 shows a relative electrode to electrode distance matrix along the Y-axis of a given lead, such as the lead shown in FIG. 4, according to the an embodiment of the present invention;

FIG. 7 shows a table enabling determination of two spatial sections by finding N-cycles according to an embodiment of the present invention;

FIG. 8 shows a R-Matrix obtained from a spinal cord model and based on system of systems of FIGS. 1 and 4, according to an embodiment of the present invention;

FIG. 9 shows a table enabling determination of two spatial sections by finding N-cycles based on R-matrix at FIG. 8, according to an embodiment of the present invention;

DETAILED DESCRIPTION OF DRAWINGS

Figure 1:
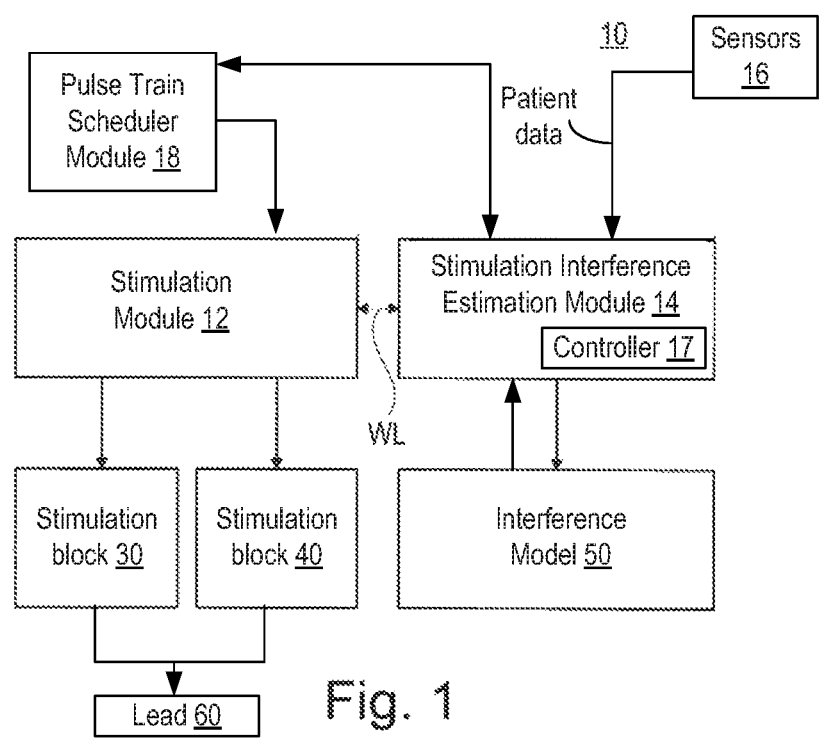
FIG. 1 shows a schematic overview of a system for multi-channel and/or variable neurostimulation according to an embodiment of the present invention.

FIG. 1 shows a schematical overview of an embodiment of the system for multi-channel and/or variable neurostimulation according to the present invention, with which the method according to the present invention can be performed.

The system 10 comprises a stimulation module 12.

In an alternative embodiment, the system comprises more than one stimulation module 12.

The system 10 further comprises a stimulation interference estimation module 14.

In an alternative embodiment, the system comprises more than one stimulation interference estimation module 14.

In this embodiment, the stimulation module 12 and the stimulation interference estimation module 14 are connected.

The connection between the stimulation module 12 and the stimulation interference estimation module 14 is in the shown embodiment a wireless and bidirectional connection WL.

However, also a cable-bound and/or unidirectional connection would be generally possible.

The stimulation module 14 provides
 a. at least a first stimulation block 30, the first stimulation block 30 comprising a first electrode configuration, a first amplitude, and a first pulse train; and
 b. at least a second stimulation block 40, the second stimulation block 40 comprising a second electrode configuration, a second amplitude, and a second pulse train.

In an alternative embodiment, the system may provide more than two stimulation blocks.

In this embodiment, the first pulse train of the first stimulation block 30 is different from the second pulse train of the second stimulation block 40.

However, it is generally possible that the first pulse train of the first stimulation block 30 is identical to the second pulse train of the second stimulation block 40.

Figure 2:
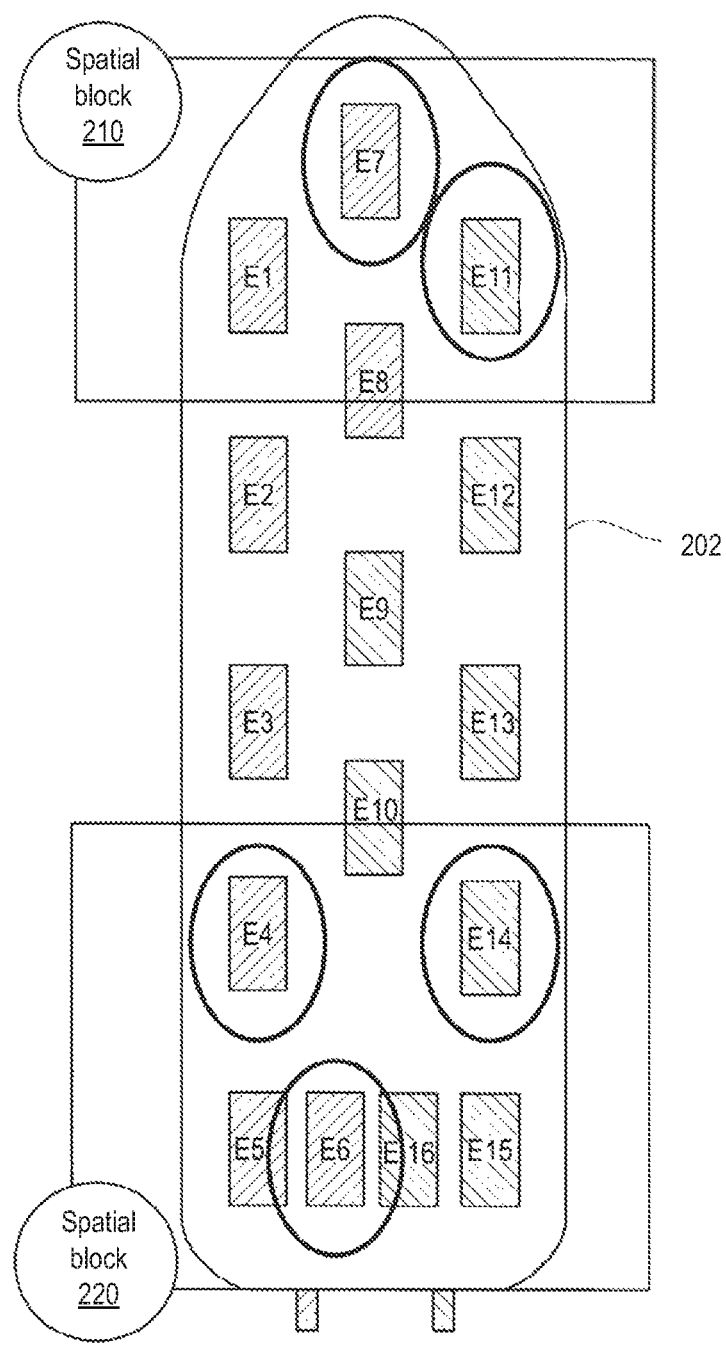
FIG. 2 shows an illustration of a lead comprising 16 electrodes for a system, such as system shown in FIG. 1, along with two example spatial sections, according to an embodiment of the present invention.
Figure 4:
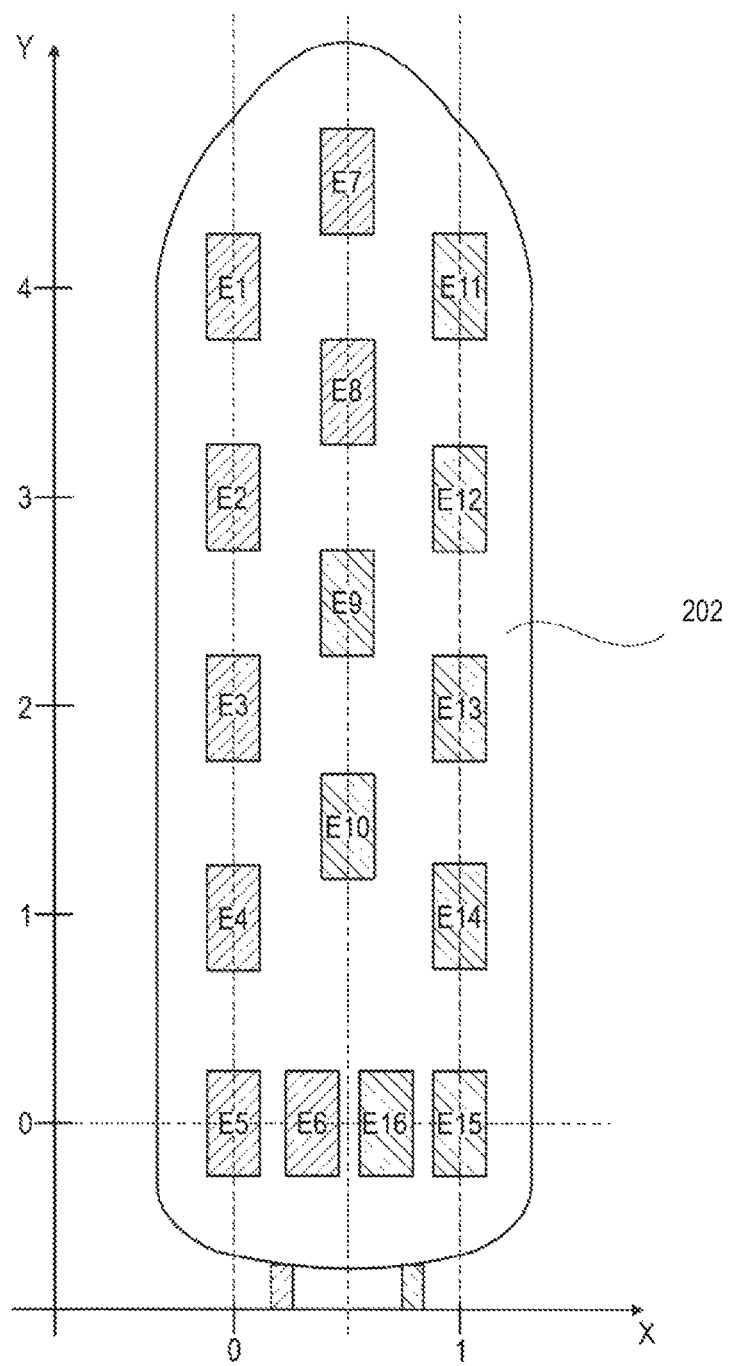
FIG. 4 shows an illustration of a lead comprising 16 electrodes designated by an electrode numbering and provided with reference axes, according to an embodiment of the present invention.

The stimulation interference estimation module 14 provides an interference model 50 for estimating the first stimulation block 30 and the second stimulation block 40 for at least one potential spatial and/or temporal overlap. In particular, the stimulation interference estimation module may include a controller 17. The controller 17, through its processors and controllers, may adjust the operation and function of the system 10. As an example, the controller 17 may adjust operation of the stimulation module 12, and a pulse train scheduler module 18 of system 10. Further, the controller 17 may receive one or more inputs, and adjust operation of one or more components of the system 10 based on the received inputs. As an example, the controller 17 may receive inputs from stimulation module 12, one or more sensors 16, and a user input, including user input regarding degree of interference (based on observed/measured rehabilitation of a patient, for example), user input regarding preferred interference model etc., from a user via a user interface included in or coupled to the system 10. In one example, based on the stimulation module input, the input including one or more stimulation blocks configurations and parameters (e.g., the specific electrodes for stimulation, configuration (e.g., unipolar, bipolar, multipolar etc.), electrode arrangement on lead, lead/electrode position on patient, etc.), controller 17 may determine an interference model that may be applied, via the controller 17, to determine interference and/or degree of interference between the intended (desired) stimulation blocks. Based on the output of the interference model, the output including the interference results, the controller 17 may adjust operation of the pulse train schedule module 18 and the stimulation module 12 to reconfigure one or more stimulation blocks, reconfiguring the stimulation blocks may include one or more of reconfiguring pulse trains of interfering stimulation blocks, current optimization of the stimulation blocks, and electrode configuration of the stimulation blocks. The one or more modified stimulation blocks may be utilized to provide neurostimulation to a patient via a lead comprising a plurality of electrodes. Example lead including a plurality of electrodes is shown at FIGS. 2 and 4. The controller 17 may also control how information, including data acquired during the operation of the system 10, is processed, displayed, stored, and manipulated. The different processing steps, including receiving one or more signals from one or more sensors, receiving user input, evaluating the received signals/input, adjusting one or more components of the system 10 to control operation of the system 10, including the methods described herein, performed by the controller 17, may be provided by a set of instructions stored in non-transitory memory of the processor. Information may also be stored in one or more non-transitory memories of controller 17 for later retrieval and use.

The system 10 comprising the stimulation module 12, the stimulation interference estimation module 14, and the pulse train scheduler module 18 may be a neurostimulation system. In one example, the neurostimulation system may be a transcutaneous system.

In another example, the neurostimulation system may be at least partially implantable or partially implanted (during treatment). Also, it can be embodied such that the system is completely/entirely implantable.

In one example, the stimulation interference estimation module can be located in the implantable part of the neurostimulation system. However, it is also possible that the stimulation interference estimation module is located in the non-implantable of the neurostimulation system. Further, the stimulation interference estimation module can be configured such that it computes the necessary adjustments in real-time and/or close to real-time.

Furthermore, the stimulation interference estimation module 14 is configured and arranged such that in case of an estimated spatial and/or temporal overlap of stimulation blocks SB, the first stimulation block 30 and/or the second stimulation block 40 are reconfigured as to avoid at least partially the spatial and/or temporal overlap of stimulation blocks.

In this embodiment, the stimulation interference estimation module 14 analyzes the spatial relationship of the first stimulation block 30 and the second stimulation block 40.

Not shown in FIG. 1 is that the stimulation interference estimation module 14 could calculate a spatial interference model of the first stimulation block 30 and the second stimulation block 40 on the basis of distance rules, R-Matrix, generic neuronal model and/or activating function model or the like.

Not shown in FIG. 1 is that the stimulation interference estimation module 14 could assess the spatial relationship of the first stimulation block 30 and the second stimulation block 40 that in case of a predetermined value indicating sufficient spatial distance between the first stimulation block 30 and the second stimulation block 40 complete temporal overlap of pulse trains is tolerated and in case of a predetermined value indicating insufficient spatial distance between the first stimulation block 30 and the second stimulation block 40 no temporal overlap of pulse trains is tolerated.

Further, system 10 includes a lead 60 comprising a plurality of electrodes through which neurostimulation is provided to a patient. In one example, upon determining interference, via stimulation interference estimation module 14, the stimulation interference estimation module 14 may reconfigure the first and/or the second stimulation blocks to reduce and/or avoid interference between the first and the second stimulation blocks. One or more parameters that may be reconfigured include 1. One or more pulse strains, including the first pulse train of the first stimulation block and/or the second pulse train of the second stimulation block; 2. One or more electrode configurations, including the first electrode configuration and/or the second electrode current of the first and the second stimulation blocks respectively; and 3. One or more stimulation currents, including a first stimulation current and a second stimulation current of the first and the second stimulation current respectively. The reconfigured stimulation blocks may be utilized to deliver neurostimulation to a patient via the lead 60 comprising a plurality of electrodes.

The system 10 may further include a pulse train scheduler (PTS) module 18. In one example, the pulse train schedule module 18 may, for a given spatial section including two or more interfering stimulation blocks, the PTS module 18 could generate pulse trains for give stimulation block, where the pulse trains match specific waveform conditions within this section. For instance, overlapping of pulse trains could be avoided for stimulation blocks which are spatially interfering, and disregarded for stimulation blocks which are not placed in the same spatial section. As an example, the stimulation interference estimation module 14 may provide pulse train reconfiguration conditions to the PTS module 18, which may then provide reconfigured pulse trains for the first and/or second stimulation blocks, via the stimulation module 12. In some embodiments, the stimulation module 12 may be configured to generate and reconfigure one or more pulse trains for the first and/or the second stimulation blocks. In further embodiments, as discussed above, the stimulation interference estimation module 14 may reconfigure one or more pulse trains.

An example is provided in FIG. 2 where two interfering spatial sections 210 and 220 of a lead 202 have been identified. Lead 202 may be an example of lead 60.

The grouping of the stimulation blocks by the stimulation interference estimation module 14 into different interfering spatial sections could be done according to the following instructions:

For combinations of the first stimulation block 30 and the second stimulation block 40 active at the same time:

If they are interfering, they could be flagged as interfering stimulation blocks.

Alternatively, if they are not interfering, they could be flagged as non-interfering stimulation blocks.

A lead 202 comprising 16 electrodes being capable to provide each an unipolar stimulation blocks designated by their electrode configuration for readability purpose is shown.

In particular five unipolar stimulation blocks designated by their lead electrode configuration for readability purpose are highlighted (circles).

The five highlighted unipolar stimulation blocks designated by their lead electrode configuration are E4, E6, E7, E11, and E14.

In this embodiment, E4, E6, E7, E11, E14 are grouped into two interfering spatial sections 210 and 220.

Not shown in FIG. 2 is that to determine the grouping, the following combinations of unipolar stimulation blocks designated by their lead electrode configuration have been considered: E7/E11, E7/E4, E7/E14, E7/E6, E11/E4, E11/E14, E11/E6, E4/E14, E4/E6, E6/E14.

In particular, the following combinations were flagged as interfering by the chosen model: E7/E11, E4/E14, E4/E6, and E6/E14.

The first interfering spatial section 210 is provided by electrode E7-electrode E11.

The second interfering spatial section 220 is provided by electrode E4-electrode E14-electrode E6.

It is generally possible that graph theory could be used to model pairwise relations between objects. A graph could made of nodes connected by edges.

In particular, each time segment (segment of the stimulation partiture during which a fixed and unique set of stimulation blocks is outputted) is associated with a graph in which the nodes are the stimulation blocks, and the edges (or lines) are linking the interfering stimulation blocks.

If a node is reachable from itself through a path of edges and nodes, then this path forms a cycle.

Figure 3:
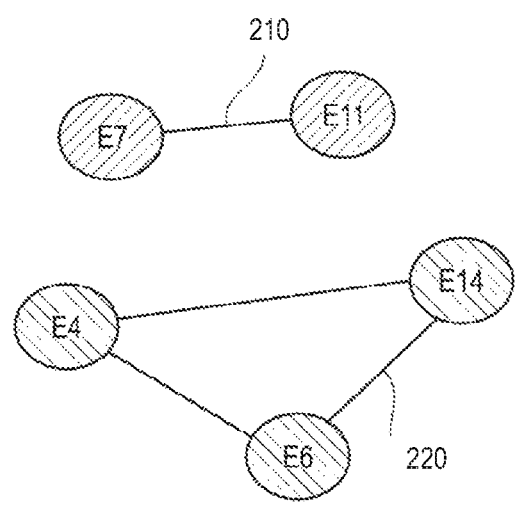
FIG. 3 shows an example graph and cycles for the spatial sections shown in FIG. 2, according to an embodiment of the present invention.

The resulting graph which leads to the grouping is shown in FIG. 3.

In the following, different embodiments of interference models 50 are described.

Interference Model Based on Distance Rules

The interference between the stimulation blocks SB could depend on many parameters, among which one is preponderant: the distance between the involved electrodes E.

In other words, the interference model 50 could be based on distance rules.

A given lead 202 (cf. FIG. 2) comprising unipolar stimulation blocks designated by their lead electrode configuration is provided with reference axes (cf. FIG. 4).

In the present embodiment, the lead 202 comprises 16 electrodes capable of providing each a unipolar stimulation block designated by their lead electrode configuration E1-E16. That is, FIG. 4 shows lead 202 including a plurality of electrodes E1-E16. In one example, each of the plurality of electrodes may be configured to provide a unipolar stimulation block. Unipolar stimulation blocks are considered for purposes of clarity. It will be appreciated that the stimulation blocks may be unipolar (as discussed herein), multipolar, or bi-polar or any combination thereof, and the various configurations of the stimulation blocks are within the scope of the disclosure.

Based on the reference axes, the relative electrode to electrode distance matrix along the X-axis (cf. FIG. 5) and the Y-axis (cf. FIG. 6) could be computed.

In the present embodiment, the absolute value of the distance is used, i.e. the absolute value of both matrix $D_X$ and $D_Y$ is considered and thus the direction is disregarded.

Two stimulation blocks will interfere if their cathodes are separated by a distance less than 0.5 on the X-axis and a distance less than 2 on the Y-axis, or by a distance less than 1 on the Y-axis, no matter the distance on the X-axis. i.e.:

$$D_X \leq 0.5 \text{ and } D_Y \leq 2$$

or $$D_Y \leq 1$$

As indicated above, the stimulation blocks are designated by their unipolar electrode configuration for readability purposes.

From FIG. 7, with respect to the five highlighted unipolar stimulation blocks designated by their lead electrode configurations E4, E6, E7, E11, E14 shown in FIG. 2, two interfering spatial sections 210, 220 are determined by finding the N-cycles, namely the 2-cycle electrode E7-electrode E11 and the 3-cycle electrode E4-electrode E14-electrode E6.

Of note, any other values may be used as a threshold-marker for an interference model 50 based on distance rules. That is, while the above example rule illustrates X-axis distance threshold as 0.5 and Y-axis distance threshold as 2, or Y-axis distance threshold as 1, other distance thresholds may be used.

An Interference Model Based on an R-Matrix

Alternatively, the interference model 50 could be based on an R-Matrix.

The R-Matrix could be used to predict the interference between the electrodes of a lead 202 (cf. FIG. 2 and/or FIG. 4) during e.g. unipolar stimulation.

In the present embodiment the R-Matrix (cf. FIG. 8) is considered computed for a 16-electrodes lead 202 (cf. FIG. 2 and/or FIG. 4) using a 3D spinal cord model.

In the present embodiment, an interference threshold must be defined.

In the present embodiment, the Interference threshold is defined as 25 Ohm.

Of note, any other values may be used as interference threshold for an interference model IM based on an R-Matrix.

For R-Values lower than 25 Ohm, the interference model 50 (R-Matrix) predicts no interference.

For R-Values above 25 Ohm the interference model 50 (R-Matrix) predicts interference.

From FIG. 9, which is based on FIG. 8, with respect to the five highlighted unipolar stimulation blocks designated by their lead electrode configurations E4, E6, E7, E11, E14 shown in FIG. 2, two spatial sections 210, 220 are determined by finding the N-cycles, namely the 2-cycle E7-E11 and the 3-cycle E4-E14-E6 (cf. FIG. 3).

In general, the R-Matrix is a transfer function between the current injected at the electrodes and the voltage induced on their surface.

For lead 210 with 16 electrodes (cf. FIG. 2 and/or FIG. 4), the equation is:

$$\begin{bmatrix} V_1 \\ \vdots \\ V_{16} \end{bmatrix} = [R_{matrix}] * \begin{bmatrix} I_1 \\ \vdots \\ I_{16} \end{bmatrix}$$

In one example, for clarity and illustration purposes, a lead with just 3 electrodes E, i.e. electrodes E1, electrodes E2 and electrodes E3 could be considered. The resulting equation is:

$$\begin{bmatrix} V_1 \\ V_2 \\ V_3 \end{bmatrix} = \begin{bmatrix} R_{11} & R_{12} & R_{13} \\ R_{21} & R_{22} & R_{23} \\ R_{31} & R_{32} & R_{33} \end{bmatrix} * \begin{bmatrix} I_1 \\ I_2 \\ I_3 \end{bmatrix}$$

If current is only injected at electrode E1 (e.g. $I_2$ and $I_3$=0), then the resulting voltage may be the first column of the R-Matrix multiplied by the current:

$$V_{I1} = \begin{bmatrix} R_{11} \\ R_{21} \\ R_{31} \end{bmatrix} * I_1$$

If the current is injected at several electrodes, then the voltages at the electrodes may be induced by the combination of the stimulation.

In one embodiment a current $I_1$ may be on electrode E1 and a current $I_2$ may be on electrode E2. The resulting voltages at electrode E1, electrode E2 and electrode E3 are:

$$V_{I1\ \&\ I2} = \begin{bmatrix} R_{11} \\ R_{21} \\ R_{31} \end{bmatrix} * I_1 + \begin{bmatrix} R_{12} \\ R_{22} \\ R_{32} \end{bmatrix} * I_2$$

A possible criterion could be that two stimulation blocks may interfere if the voltage variation induced on the injecting electrodes (i.e. cathodes) is larger than a certain threshold.

A possible criterion could be that two stimulation blocks SB may interfere if the voltage variation induced on the injecting electrodes E (i.e. cathodes) is larger than 10%.

A possible embodiment could be the following R-Matrix with an injected current of 3 mA at electrode E1 (stimulation block SB 1, unipolar) and of 2 mA at electrode E2 (stimulation block SB 2, unipolar).

Accordingly, the voltages when the injection is orthogonal or simultaneous could be:

$$R = \begin{bmatrix} 750 & 35 & 15 \\ 20 & 740 & 15 \\ 40 & 20 & 705 \end{bmatrix}$$

$$V_{SB1\text{-}alone} = \begin{bmatrix} 2250 \\ 60 \\ 120 \end{bmatrix}$$

$$V_{SB2\text{-}alone} = \begin{bmatrix} 70 \\ 1480 \\ 40 \end{bmatrix}$$

$$V_{combination} = \begin{bmatrix} 750 & 35 & 15 \\ 20 & 740 & 15 \\ 40 & 20 & 705 \end{bmatrix} * \begin{bmatrix} 3 \\ 2 \\ 0 \end{bmatrix} = \begin{bmatrix} 2320 \\ 1540 \\ 160 \end{bmatrix}$$

The voltage variation induced by the overlap is 70 (3.11% of 2250) and 60 (4.05% of 1480) mV at electrode E1 and electrode E2, respectively.

The voltage variation is lower than 10% so according to the mentioned criterion the two stimulation blocks SB1 and SB2 do not interfere.

For multipolar electrode configuration, a second criterion may be added to characterize the variation at the anodes.

In some examples, a system with any number of electrodes E, i.e. E1-EN could be considered.

Of note, the threshold must not necessarily be 10% but could also be set lower or higher than 10%.

An Interference Model Based On Neuronal Stimulation

The interference model 50 could also be defined at the level of the nerve fibers, i.e. based on neural stimulation.

Pulse overlapping could alter the expected firing rate of the targeted nerve fibers.

Two overlapping stimulation blocks do not interfere if the firing rate of the targeted nerve fibers remains within a tolerance margin to the expected firing rate due to the stimulation blocks taken alone.

In one embodiment a time segment lasting for a fixed amount of time T, during which a stimulation on electrode E1 (first stimulation block) which should trigger N1 action potentials on lumbar segment L1 and a stimulation on electrode E4 (second stimulation block) which should trigger N2 action potentials on lumbar segment L5 are outputted, with a tolerance margin of ±10%. If the combination of the stimulation on electrode E1 and electrode E4 generates between $N_1-10\%$ and $N_1+10\%$ action potentials on lumbar segment L1, and $N_2-10\%$ and $N_2+10\%$ action potentials on lumbar segment L5 during the duration T, then the two stimulation blocks, the first and the second stimulation blocks, do not interfere.

Figure 10:
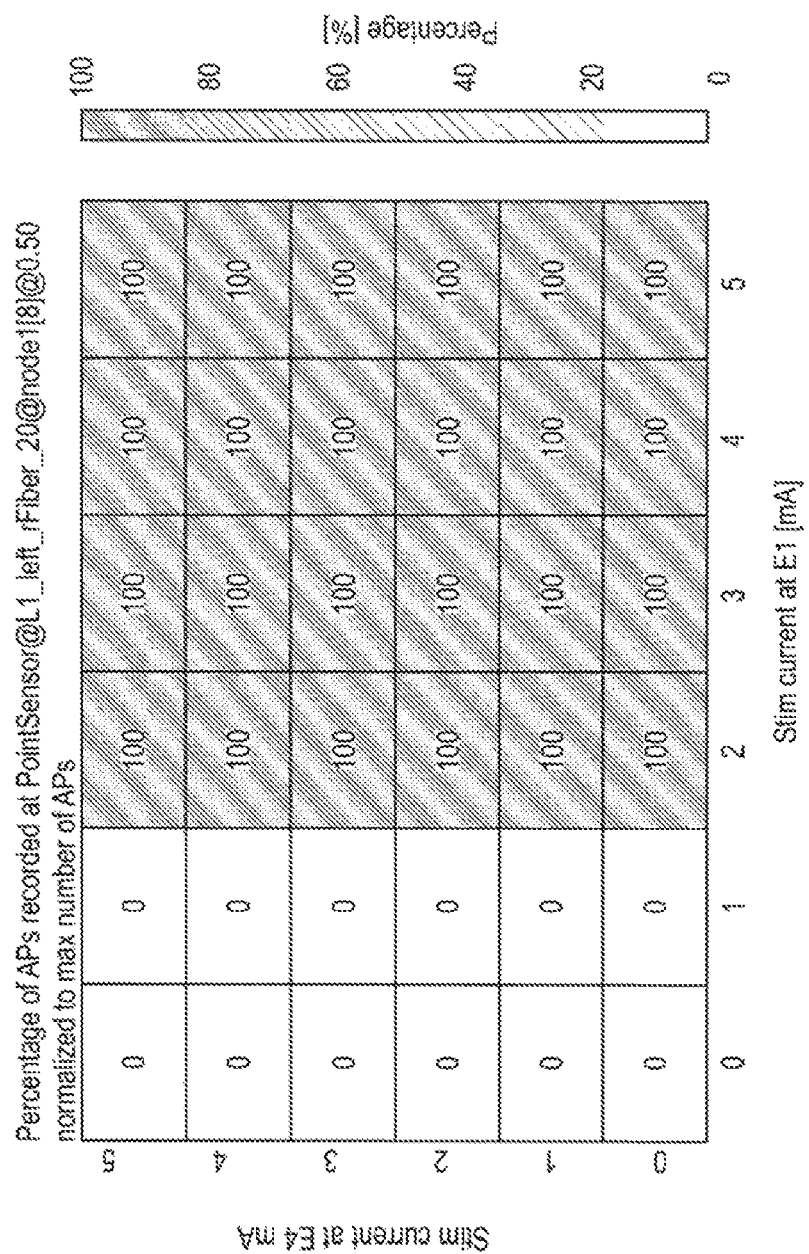
FIG. 10 shows a heat map of recorded action potentials at lumbar segment L1 left fiber for stimulation current at electrode E1 and electrode E4, according to an embodiment of the present invention.
Figure 11:
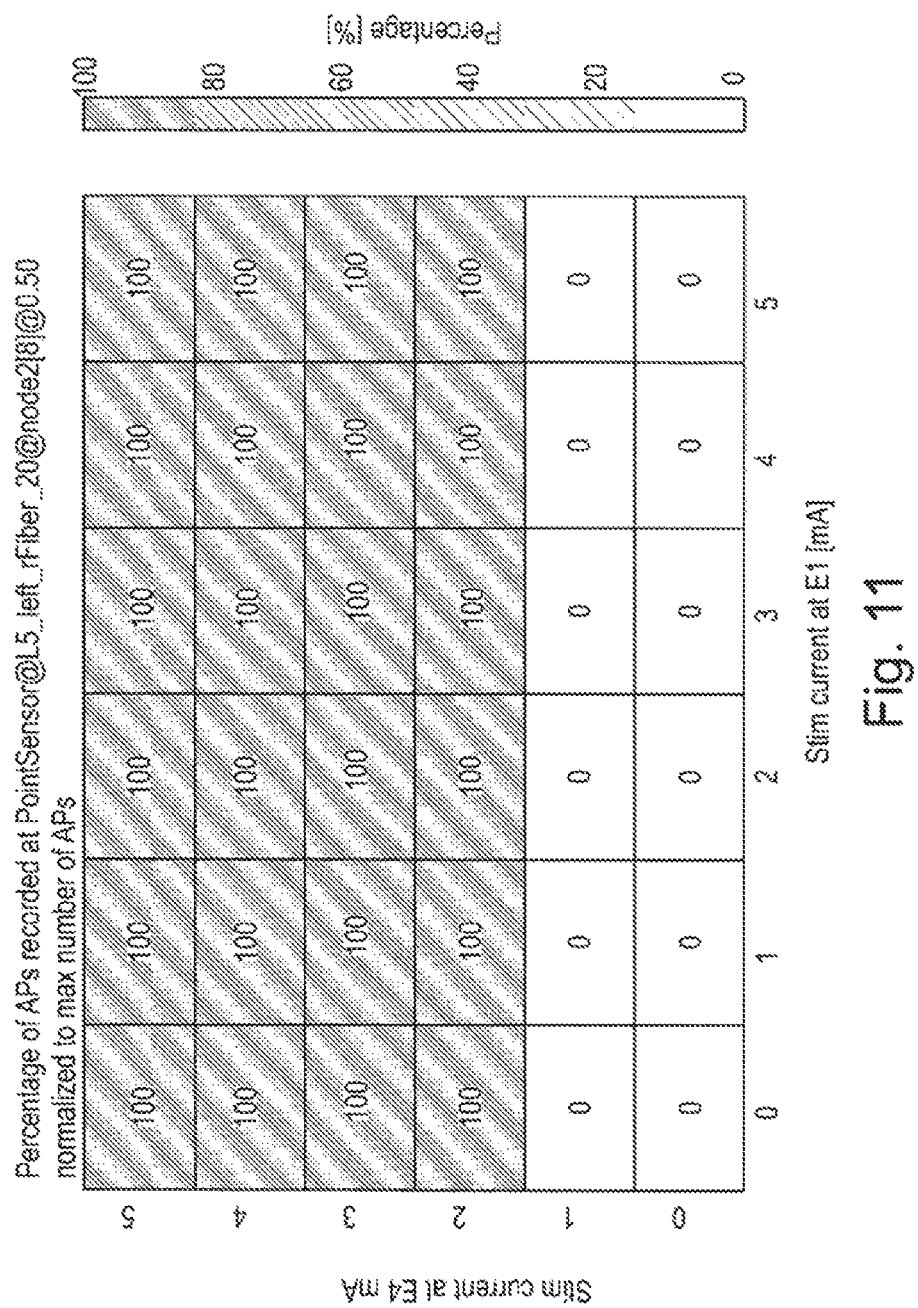
FIG. 11 shows a heat map of recorded action potentials at lumbar segment L5 left fiber for stimulation current at electrode E1 and electrode E4, according to an embodiment of the present invention.

On the corresponding heatmap of recorded action potentials (APs) at lumbar segment L1 and lumbar segment L5 (cf. FIG. 10 and FIG. 11) where eight action potentials are expected at lumbar segment L1 and 10 action potentials are expected at lumbar segment L5 from the stimulation between 0 and 5 mA at electrode E1 and electrode E4 by the first stimulation block and second stimulation block, the correct number of action potentials is outputted on both fibers thus the two unipolar stimulations blocks do not interfere for the considered current levels.

Figure 12:
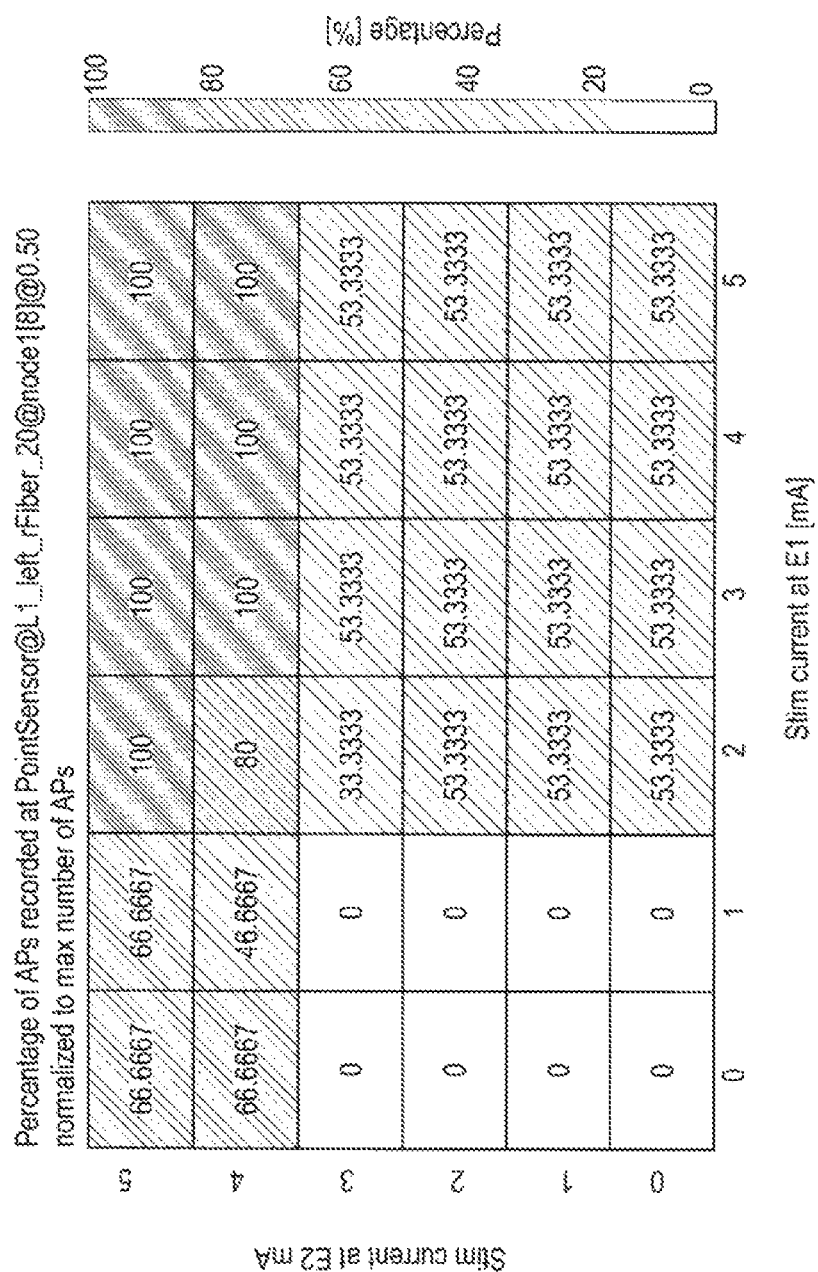
FIG. 12 shows a heat map of recorded action potentials at lumbar segment L1 left fiber for stimulation current at electrode E1 and electrode E2, according to an embodiment of the present invention.
Figure 13:
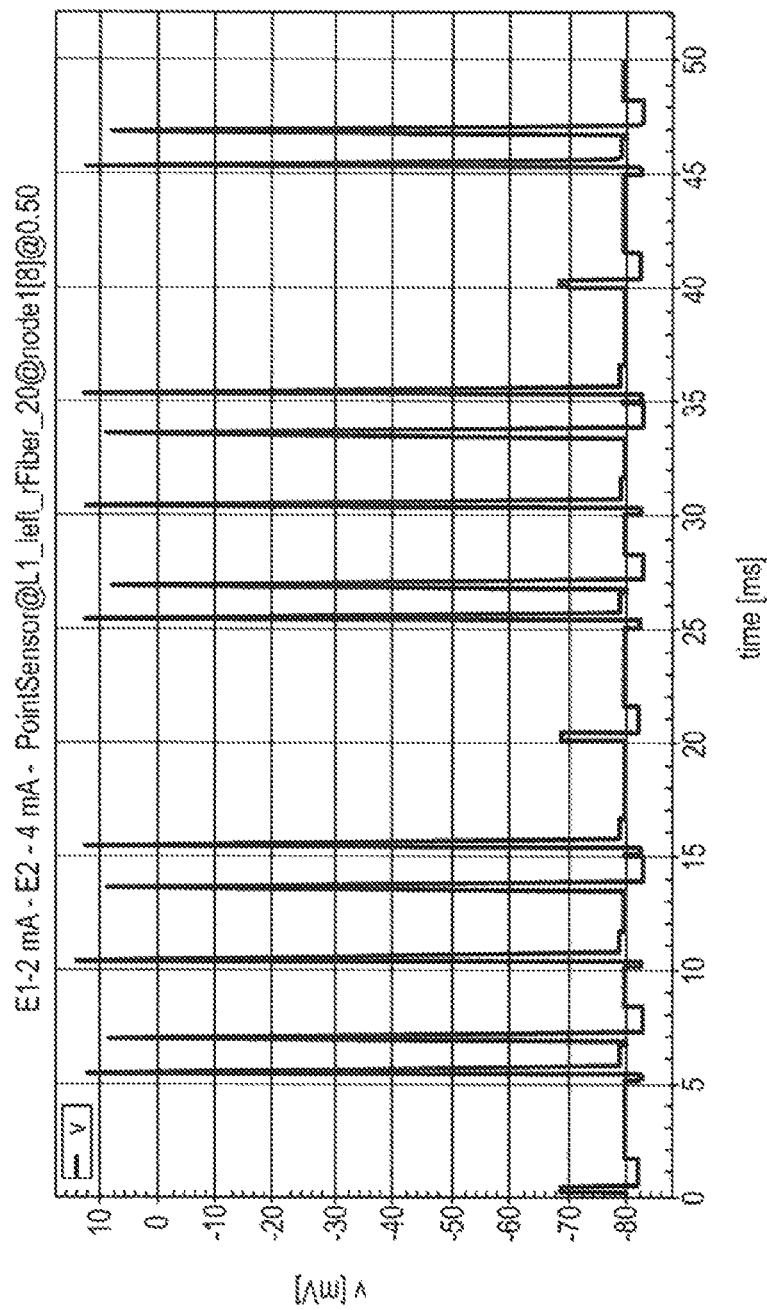
FIG. 13 shows an example graph illustrating membrane potential at point sensor along lumbar segment L1 left fiber for 2 mA at electrode E1 and 4 mA at electrode E2, according to an embodiment of the present invention.

In an embodiment with nearby electrodes, the interference becomes stronger. The heatmap of recorded action potentials at lumbar segment L1 left fiber for stimulation current at electrode E1 (first stimulation block) and electrode E2 (third stimulation block) between 0 and 5 mA (cf. FIG. 12) shows that the stimulation on electrode E2 by the third stimulation block triggers unwanted action potentials on lumbar segment L1 left (cf. FIG. 13; Membrane potential at point sensor along L1 left fiber for 2 mA at E1 and 4 mA at E2. Undesirable action potentials are triggered. In this case, interference between the stimulations blocks is acknowledged).

In some example, neuronal simulations, for example on 3D spinal cord models, may be utilized to estimate the action potentials.

Moreover, a criterion on the action potentials triggering on the non-targeted fibers might be considered. It could be generally possible that, if more than 5% of the total action potentials triggering takes places on non-targeted fibers, then interference between the stimulations blocks is acknowledged.

In general, any value could be considered as threshold.

An Interference Model Based on the Activating Function

The interference could be defined in terms of an activating function. The activating function is proportional to the second derivative of a potential field along a nerve fiber and it is a very good indicator of the likelihood that the nerve fiber will fire in response to an applied electric field. An action potential is triggered where the activating function is above a certain threshold. This threshold is unique for each fiber and can be estimated through neuronal simulations.

In some examples, neuronal stimulations may be used wherein membrane potential of each fiber may be determined from point sensors and used to determine if action potential is triggered corresponding to the applied electric field (stimulation).

Figure 15:
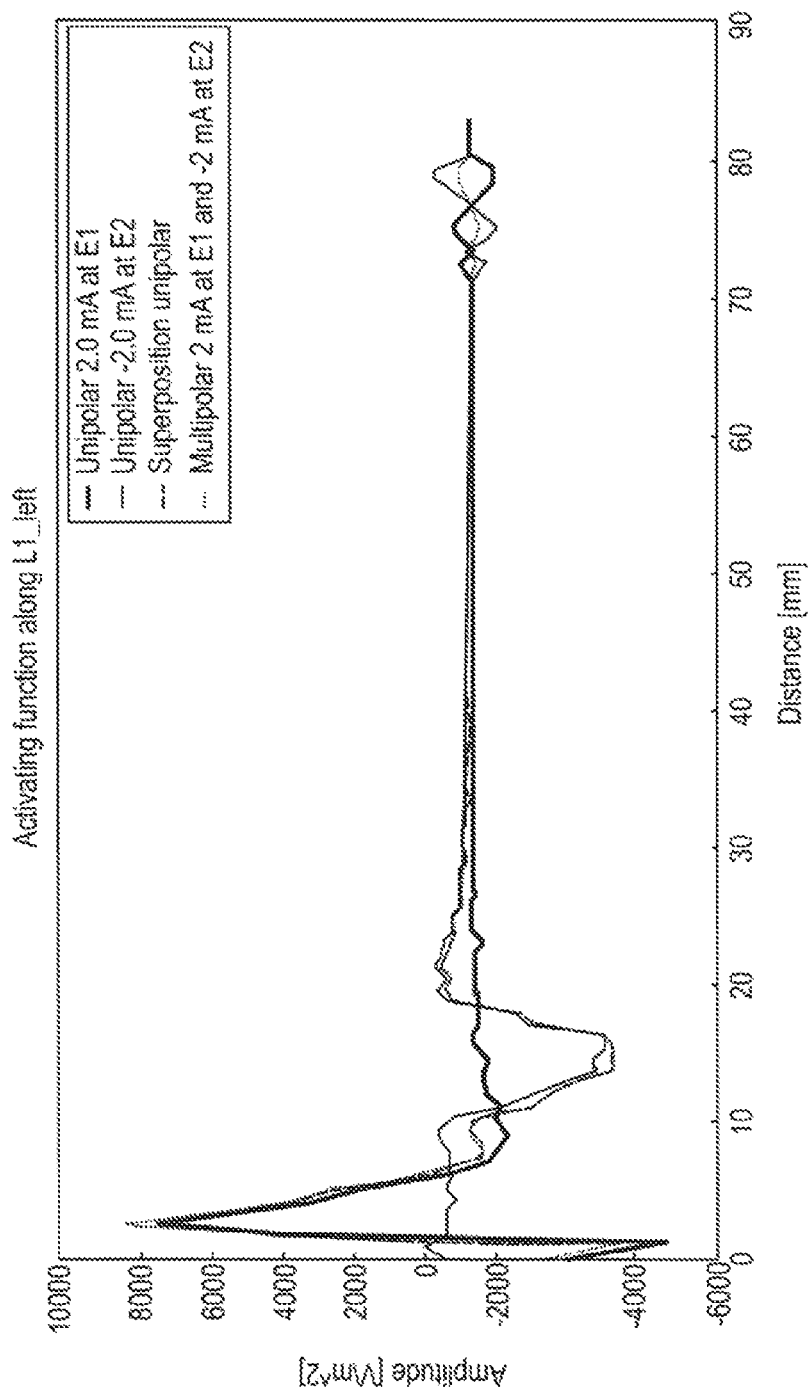
FIG. 15 shows an example of activating function for two unipolar stimulation on electrode E1 and on electrode E2 and of the activating function resulting from the superposition of both unipolar stimulation, according to an embodiment of the present invention.

A transfer function between each unipolar stimulation and the second derivative of the potential field along the targeted fibers could be computed. Since the system is linear, the second derivative of the potential field induced by any combination of unipolar stimulations can be deduced from the first set and used to estimate the interference between stimulations. Thus, any stimulation block (unipolar but also multipolar) activating function can be composed/calculated from the unipolar stimulation activating function of each active electrode of the stimulation block and used to determine interference through superposition (cf. FIG. 15; Example of activating function for two unipolar stimulation on electrode E1 (2 mA) and on electrode E2 (−2 mA). The superposition of both activating function is similar to the activating function resulting from the equivalent multipolar configuration).

Figure 14:
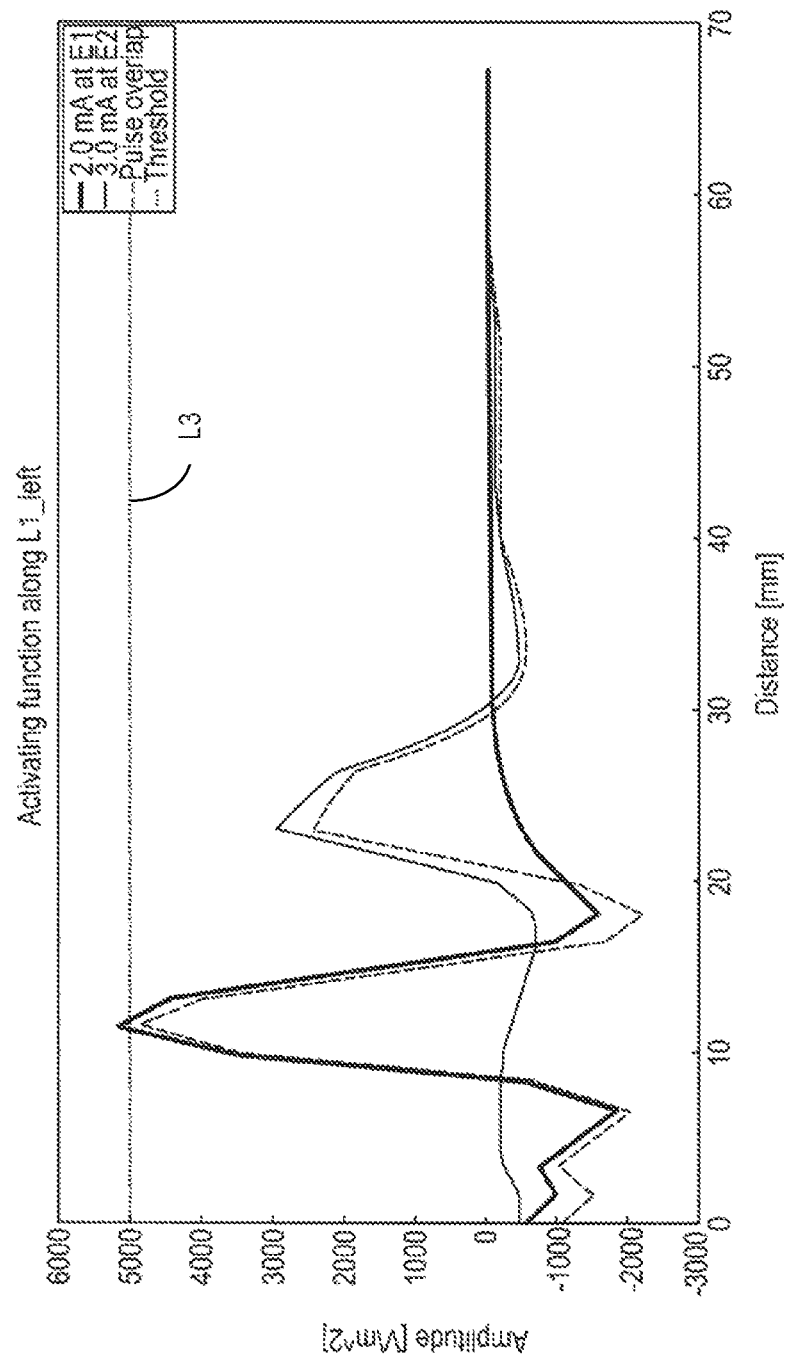
FIG. 14 shows an example of activating function for two unipolar stimulation on electrode E1 and on electrode E2 where the activating function shows destructive interference, according to an embodiment of the present invention.

If the activating function calculated along fibers targeted by two different stimulation blocks is below the threshold when the stimulation blocks are orthogonal but it is raised above the threshold when the two stimulation blocks overlap, then constructive interference between the two stimulation blocks is acknowledged. On the other hand, if the activating function calculated along fibers targeted by two different stimulation blocks is above the threshold when the stimulation blocks are orthogonal but it is lowered below the threshold when the two stimulation blocks overlap, then destructive interference between the two stimulation blocks SB is acknowledged (cf. FIG. 14, example of destructive interference; the activating function along lumbar segment L1 left fiber is calculated for 2.0 mA at electrode E1 (black line=line L1), 3.0 mA at electrode E2 (black dashed line=line L2). The threshold of activation was computed from the neuronal simulation and set to 5000 V/m$^2$ (grey dotted line=line L3). The peak of the activating function for electrode E1 is larger than the threshold, therefore the fiber will fire an action potential. However, if the pulses at electrode E1 and electrode E2 overlapped, the resulting activating function AF (grey line=line L4) would be lowered below the threshold preventing the fiber to fire).

A criterion on the non-targeted fibers could also be considered. For instance, if two stimulations blocks have their activating functions above the threshold along both targeted fibers and the combination induce an activating function above the threshold along a non-targeted fiber, then interference is acknowledged.

As for the neuronal stimulation model, this model can be applied with a tolerance margin during a time segment. If the activating functions AF resulting from the superposition of two stimulations blocks SB are impacted by interference (constructive or destructive) less than e.g. 10% of the time, the combination of these two stimulation blocks could be flagged as not interfering during this specific time segment.

Non-Boolean Model

In general, a Boolean model could be applied for all interference models IM described.

Alternatively, a Non-Boolean model could be applied for all models described.

In particular, the Non-Boolean model could define several degrees of interference which would be attached to several degrees of freedom in the temporal domain.

In other words, with regard to FIG. 1, the stimulation interference estimation module 14 could be configured and arranged to assess the spatial relationship of the first stimulation block 30 and the second stimulation block 40, that in case of a predetermined degree of spatial interference between the first stimulation block 30 and the second stimulation block 40 a predetermined degree of freedom is tolerated for a temporal overlap of pulse trains.

In one example, a threshold on an R-Matrix (cf. FIG. 8) is considered.

The 3 following levels of interference could be defined:
Interference is defined for values above 25;
Slight interference is defined for values between 10 and 25; and
No interference is defined for values below 10.

Then, different degrees of overlap could be allowed in the temporal domain:
If two or more stimulation blocks interfere no overlapping is allowed between the pulses;
If two or more stimulation blocks slightly interfere, no overlapping of the cathodic phase (stimulation) with the anodic phase (post-stimulation) is allowed if the stimulation blocks are not sharing electrodes; and If two or more stimulation blocks do not interfere overlapping is allowed if the stimulation blocks are not sharing electrodes.

From the interference procedure defined above, and depending on the model chosen, a more complex definition of the interference could be applied. A 2D matrix could be computed with each matrix value weighing the interference between the stimulation block. This could be extended to an N-dimensional matrix (each axis represents all the individual stimulation block) to cover combinations of stimulation blocks.

Moreover, this interference matrix could be customizable by the user.

In particular, a matrix computed from simulation could then be modified by the user if additional knowledge obtained through rehabilitation shows that assumed interfering stimulation blocks do not interact one with the other at an intolerable level. The other way around, two stimulation blocks which have a low interference weighting could be manually flagged as interfering by the user.

Patient Specific Model

In general, the different embodiments of an interference model 50 described could be a generic model.

Alternatively, the different embodiments of an interference model 50 can be made patient-specific.

In particular, the different embodiments of an interference model 50 can be made patient-specific based on patient data.

Patient data could include any type of data indicating patient anatomy and/or physiology.

For instance, the neuronal simulation could be performed with a patient-specific spinal cord model created from magnetic resonance imaging (MRI) data and/or computer tomography (CT) data or similar data to determine the anatomy of the spinal cord and the placement of the lead(s) L, respectively.

For the R-Matrix, it could be directly measured on the patient through an implantable pulse generator (IPG) measurement procedure.

Another possibility to personalize the interference model to specific patients lies in electromyography (EMG) measurements.

In particular, muscle response induced by the overlapping of two stimulation blocks could be measured.

Each combination of two stimulation blocks could be tested, and a recruitment curve and a selectivity index induced by the overlapping of stimulation blocks could be compared to a second recruitment curve and a second selectivity index induced by orthogonal stimulation.

In one embodiment, a first stimulation block has a selectivity index of 1 on the hip flexion (i.e. perfectly selective) and a second stimulation block has a selectivity index of 1 on the knee extension. Whenever the first stimulation block and the stimulation block overlap, the selectivity indices are likely to change. A criterion is chosen to detect interference: if the selectivity index for the hip flexion and for the knee extension falls below 0.8, then interference is acknowledged.

In general, every other value for the selectivity index could be considered interference.

Moreover, a criterion on the selectivity index of the non-targeted muscle group could be considered. For example, an increase in the selectivity index of more than 10% on the non-targeted stimulation blocks is considered interference.

The pulse train and/or electrode configuration and/or stimulation currents of the first stimulation block 30 and/or the second stimulation block 40 could be reconfigured.

Pulse Train Reconfiguration

The spatial segmentation could be combined or integrated with a pulse train scheduler module (PTS), such as PTS module 18 at FIG. 1. On each spatial section S, the PTS could match specific waveform conditions within this section. For instance, overlapping could be avoided for stimulation blocks which are spatially interfering, and disregarded for stimulation blocks which are not placed in the same spatial section.

Moreover, the PTS could also be used to minimize the impact of each spatial section on the others.

It could be used to delay the output of a complete section, or some of the waveforms in a section, with respect to the other sections in order to minimize a parameter, such as the amount of overlap. Moreover, instead of matching conditions for stimulation blocks within a spatial section, it could also be used in a way that would check conditions between the spatial sections such as forbidding overlap between the stimulation phases of the pulses from section S1, such as section 210, with the stimulation phase of the pulses from section S2, such as section 220.

Current Optimization

Predicting interference could also be used to optimize the injected current for the therapy.

In one embodiment using activating function as interference model 50, the difference between the maximum value of the activating function and the threshold determines the amount of injected current that is needed to reach the threshold and trigger the action potential, or that can be reduced to save battery lifetime without altering the therapeutic effect.

This current optimization could be either performed in real-time or beforehand by a method looking through the planned stimulation and optimizing the current for each pulse individually.

Electrode Configuration Optimization/Tuning

When interference is detected, the specific electrode configurations per stimulation blocks could be optimized to minimize the effect of interference while keeping the activation of the targeted fiber. For example, for interference involving two unipolar stimulation blocks, one of the stimulation blocks SB could have its electrode constellation changed to a multipolar setting shielding the cathode and preventing interference.

Electrode reconfiguration could also be considered to overcome hardware limitations.

For instance, if two stimulation blocks SB have their electrode configurations sharing an electrode, the stimulation hardware might not be able to generate the (superposition) pattern of currents if the two stimulation blocks SB have overlapping pulses;

if pulses need to be output too close in time, the stimulation engine might not be able to change its output current amplitude fast enough to accommodate the newly required current.

An alternative suboptimal electrode configuration could be proposed for one or for both stimulation blocks so that the hardware is capable again to generate the desired stimulation pulses/patterns. The interference induced by the new electrode configurations could be reassessed and the spatial sections could be updated accordingly.

Another option to use electrode reconfiguration could be to minimize the impact of interference when overlap occurs. For example, at the cost of less specificity, if a suboptimal (from the perspective of selectivity) alternative electrode configuration or configurations are chosen that still perform better than the originally chosen electrode configurations during interference.

This optimization of the electrode configuration could be performed either beforehand or in real-time as the stimulation engine generates the desired waveforms.

Closed-Loop Behaviour

The methods and systems described herein could be used in a close-loop fashion, taking into account exterior parameters to compute interference.

For instance, a sensor system could be coupled and used to compute an interference matrix in real-time to dynamically consider the effect of patient data on the interference between the stimulation blocks. This could provide the possibility to allow or not allow interference in a given posture or to adjust the interfering stimulation block parameters (stimulation amplitude, electrode configuration, etc.) in real-time.

However, the methods and systems described herein could also be used in an open-loop fashion.

Grounded Electrode Interference

The previous embodiments only consider the active stimulation blocks and their active electrodes. However, grounded electrode(s) (i.e. connected to ground (GND)) could have an impact on the electrical field, and thereby on the nerve fiber recruitment and the stimulation. Grounding of electrodes usually takes place after each stimulation pulse of a stimulation block to remove any residual injected charge, for example, due to the inherent imbalance between stimulation and post-stimulation pulse parts of a biphasic pulse. During this grounding phase, electrodes could be shorted to system GND or can be shorted together instead. The housing of the IPG could be included in this grounding activity, for example, in case of unipolar stimulation, where the housing can be shorted to (system) GND or to the stimulation electrode(s) instead.

The interference induced by the grounded electrode(s) and/or IPG housing during the grounding phase can be assessed in the same way as for the stimulation blocks. For instance, a distance criterion could be applied between the active electrode of a stimulation block and the grounded electrode(s). If the grounded electrode(s) are too closed to the active electrodes of a given stimulation block and indeed interfere, they are placed in the same spatial section as the given stimulation block. Further optimization is then performed according to the spatial section. For instance, the current delivered by the stimulation blocks in the spatial section can be optimized to counter balance the effect of the grounded electrodes.

If it turns out that a grounding phase does not lead to interference, this phase can be run in parallel to active stimulation and as such enables a higher pulse budget, that is, a higher number of pulses that can be output per unit of time.

Figure 16:
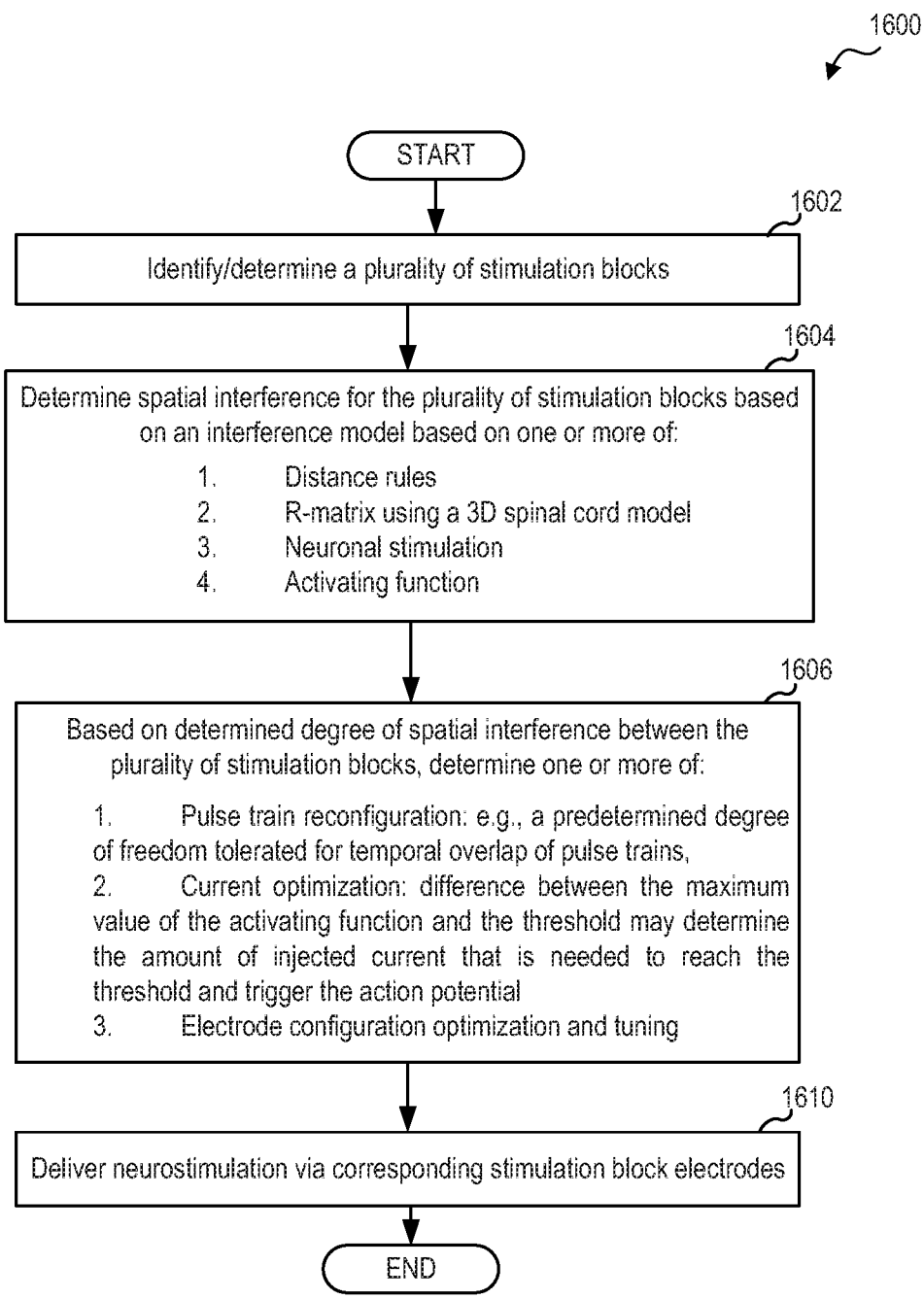
FIG. 16 shows a flow chart illustrating a high-level method for determining interference among a plurality of stimulation blocks, and reconfiguring one or more parameters of interfering stimulation blocks, according to an embodiment of the present invention.

FIG. 16 shows a flow chart illustrating a high-level method 1600 for determining spatial interference among a plurality of stimulation blocks of a lead comprising a plurality of electrodes, such as lead 202 at FIG. 2. While present method 1600 is described for open-loop control, the method 1600 may be modified to achieve closed loop control. For example, the closed loop control may take into account exterior parameters to compute the interference matrix. For instance, a posture detection system could be coupled (either through inertia measurement units or e.g. impedance measurement or any other type of sensor) and used to compute an interference matrix in real-time to dynamically consider the effect of posture on the interference between the stimulation blocks.

Method 1600 may be implemented by a processing system, such as controller 17 at FIG. 1, or one or more processing systems in communication with the processing system, or any appropriate combination thereof. Further, the method 1600 may be implemented by controller 17 in conjunction with modules and components of system 10, such as stimulation module 12 and pulse train scheduler module 18. Furthermore, in some examples, one or more modules and components of system 10, such as the stimulation module 12, or the pulse train scheduler module 18 may be configured to implement the method 1600 based on instructions stored in non-transitory memory, in conjunction with other modules of the system. Method 1600 is described with regard to the systems and components of FIGS. 1 and 2, although it should be appreciated that method 1600 may be implemented with other systems and components without departing from the scope of the present disclosure.

At 1602, the method 1600 includes determining and/or identifying a plurality of stimulation blocks to be applied via a lead including plurality of electrodes (e.g., lead 202 at FIG. 2) during neurostimulation for a patient, using a neurostimulator system, such as system 10 of FIG. 1. In one example, the stimulation blocks may be determined via a stimulation module, such as stimulation module 12 at FIG. 1. For example, the stimulation block may provide an electrode configuration, an amplitude/intensity of stimulation and a pulse train, Thus, for neurostimulation involving a gait cycle, a plurality of stimulation blocks may need to be stimulated simultaneously with different pulsed electrical waveforms at different frequencies and amplitudes, sometimes with different pattern of pulses, in order to reproduce a movement, e.g. cycle comparable to a healthy subject.

Next, at 1604, the method 1600 includes determining spatial interference between the plurality of stimulation blocks. For example, the stimulation interference estimation module 14, based on the plurality of stimulation blocks provided by the stimulation module 12, may determine interference between the plurality of stimulation blocks.

In one example, the stimulation interference module 14 may determine one or more spatial blocks, each including interfering stimulation blocks. Example spatial blocks are spatial blocks 210 and 220 in FIG. 2, where spatial block 210 includes two interfering stimulation blocks provided via unipolar electrodes E7 and E11 and spatial block 220 includes three interfering stimulation blocks provided via unipolar electrodes E4, E6, and E14 (where E4, E6, E7, E11 and E14 are electrodes of lead 202). The interfering stimulation blocks, and thus the spatial blocks, are determined based on an interference model, such as interference model 50 at FIG. 1. As discussed above, the interference model may be configured to be patient-specific, based on patient imaging data, and measurements from a patient (e.g., measurements for R-matrix, EMG measurements etc.). In some examples, the interference model may be configured to be generic.

In one example, the interference model is based on distance rules. The distance rule is based on the reference axes for the electrodes of the lead, such as reference axes shown at FIG. 4. In particular, the relative electrode to electrode distance matrix along the X-axis (cf. FIG. 5) and the Y-axis (cf. FIG. 6) may be computed. In one example, the interference may be determined based on a distance rule: two stimulation blocks will interfere if their cathodes are separated by a distance less than 0.5 on the X-axis and a distance less than 2 on the Y-axis, or by a distance less than 1 on the Y-axis, no matter the distance on the X-axis. An example is shown in FIG. 7 with respect to the five highlighted unipolar stimulation blocks designated by their lead electrode configurations E4, E6, E7, E11, and E14 shown in FIG. 2. Two interfering spatial sections 210, 220 are determined based on distance rules by finding the N-cycles, namely the 2-cycle electrode E7-electrode E11 and the 3-cycle electrode E4-electrode E14-electrode E6. In one example, the placement of lead and the electrodes may be determined based on patient imaging data, and thus may be patient specific. Generic electrode and lead positioning and spinal cord anatomy are also within the scope of the disclosure.

In another example, the interference model is based on an R-matrix using a 3D spinal cord model. As discussed above, R-matrix is a transfer function between the current injected at the electrodes and the voltage induced on their surface. An example R-matrix computed using a 3D spinal cord model for the 16 electrodes of lead 202 is shown at FIG. 8. FIG. 9 is based on FIG. 8, and shows the spatial blocks 210 and 220 (also referred to as spatial sections) identified with respect to the five highlighted unipolar stimulation blocks designated by their lead electrode configurations E4, E6, E7, E11, and E14 shown in FIG. 2. In this example, an interference threshold of 25 Ohms is used to determine the interfering stimulation blocks. In another example, that two stimulation blocks may be considered to interfere if the voltage variation induced on the injecting electrodes (i.e. cathodes) is larger than a certain threshold, where the voltage variation is based on the R-matrix, a size (number of rows by number of columns) of the R-matrix based on a number of electrodes. In some examples, the R-values for the R-matrix may be directly measured on the patient through an implantable pulse generator (IPG) measurement procedure for various electrode combinations. Further, the spinal cord model may be generated from patient imaging data (e.g., CT, MRI etc.) and thus, may be patient specific. However, in some examples, the spinal cord model may be generic.

In yet another example, the interference model is based on neuronal stimulation. As discussed above with respect to FIGS. 10-13, the interference model based on neuronal stimulation may be determined by number of action potentials outputted on specific spinal segments and/or nerve fibers. The action potentials may be determined based on membrane potential determined from point sensors. For example, the stimulation interference module 14, via the controller 17, may receive input from one or more point sensors coupled to one or more spinal segments of the patient, and action potentials recorded at the one or more spinal segments (lumbar segment L1 left fiber) at given stimulation current or currents within a current range at two or more stimulation blocks (e.g. electrode E1, electrode E2, etc.) may be utilized to determine interference between the stimulation blocks.

In still further example, the interference model may be based on an activating function. In this model, a difference between a maximum value of the activating function and a threshold may determine an amount of injected current that is needed to reach the threshold and trigger an action potential is utilized. As discussed above with respect to FIGS. 14 and 15, a second derivative of a potential field induced by any combination of unipolar stimulations can be used to estimate the interference between stimulations. Thus, any stimulation block (unipolar but also multipolar) activating function may be composed/calculated from the unipolar stimulation activating function of each active electrode of the stimulation block and used to determine interference through superposition.

Next, at 1606, the method 1600 includes reconfiguring one or more parameters of the stimulation blocks. In one example, one or more interfering stimulation blocks, such as a first stimulation block and/or second stimulation block, may be reconfigured to reduce at least partially the spatial and/or temporal overlap of stimulation blocks.

Reconfiguring one or more stimulation blocks may include pulse train reconfiguration. In one example, a predetermined degree of freedom for temporal overlap of pulse trains may be tolerated. In another example, pulse train overlapping could be avoided for stimulation blocks that are spatially interfering, and disregarded for stimulation blocks that are not placed in the same spatial section.

Reconfiguring one or more one or more stimulation blocks may include optimizing injected current. In one example, using activating function as interference model, a difference between the maximum value of the activating function and the threshold may determine the amount of injected current that is needed to reach the threshold and trigger the action potential, or that can be reduced to save battery lifetime without altering the therapeutic effect.

Reconfiguring one or more stimulation blocks may include electrode configuration optimization. For example, as discussed above, for interference involving two unipolar stimulation blocks, one of the stimulation blocks could have its electrode constellation changed to a multipolar setting shielding the cathode and preventing interference. It will be appreciated that electrode reconfiguration could also be considered to overcome hardware limitations.

Upon reconfiguring various interfering stimulation blocks to reduce and/or avoid overlapping and/or interference, neurostimulation may be delivered to the patient via corresponding electrodes of the lead.

A technical effect of determining interference between stimulation blocks and reconfiguring one or more parameters of the stimulation blocks includes reduced or complete avoidance of spatial and/or temporal overlap of the pulse trains of different stimulation blocks This results in improved neurostimulation in a more controlled fashion, for example, efficient stimulation of the desired (target) areas and in a secure way (e.g., without overstimulating and by reducing stimulation of non-target areas), while drawing as little power as possible from the battery.

Note that the example control and estimation routines included herein can be used with various system configurations. The control methods, routines and models disclosed herein may be stored as executable instructions in non-transitory memory and may be carried out by a system 10 as described above, either by the whole system or any other system hardware or modules of the system. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of a computer readable storage medium in the system 10, or any of its modules, where the described actions are carried out by executing the instructions in the system 10 including the various hardware components.

REFERENCES

10 System for a multi-channel and/or variable neurostimulation
12 Stimulation module
14 Stimulation interference estimation module
16 Sensors
17 Controller
18 Pulse train scheduler
50 Interference model
202 Lead
AF Activating function
$D_X$ Distance on x-axis
$D_Y$ Distance on y-axis
E Electrode
E1 Electrode 1
E2 Electrode 2
E3 Electrode 3
E4 Electrode 4
E5 Electrode 5
E6 Electrode 6
E7 Electrode 7
E8 Electrode 8
E9 Electrode 9
E10 Electrode 10
E11 Electrode 11
E12 Electrode 12
E13 Electrode 13
E14 Electrode 14
E15 Electrode 15
E16 Electrode 16
30 Stimulation block 1
40 Stimulation block 2
SB3 Stimulation block 3
SBN Stimulation block N
210 Interfering spatial section 1
220 Interfering spatial section 2
WL Wireless link/wireless connection

The invention claimed is:

1. A neurostimulation system comprising:
at least one stimulation module for providing stimulation blocks, the stimulation blocks including:
at least a first stimulation block, the first stimulation block comprising a first electrode configuration, a first amplitude, and a first pulse train, and
at least a second stimulation block, the second stimulation block comprising a second electrode configuration, a second amplitude, and a second pulse train; and
at least one stimulation interference estimation module including a controller configured with instructions in non-transitory memory that when executed cause the controller to:
construct a graphical representation of interference relationships between the stimulation blocks, the graphical representation including:
nodes representing the stimulation blocks, a first node representing the first stimulation block and a second node representing the second stimulation block; and
edges connecting the nodes, a first edge connecting the first node to the second node indicating interference between the first stimulation block and the second stimulation block;
identify a first spatial section including the first node and the second node using the graphical representation; and
in response to the identification of the first spatial section, reduce interference between stimulation blocks corresponding to the nodes in the first spatial section by reconfiguring at least one of the first stimulation block or the second stimulation block.

2. The system of claim 1, wherein constructing the graphical representation comprises:
analyzing a spatial relationship between the first stimulation block and the second stimulation block.

3. The system of claim 2, wherein constructing the graphical representation comprises:
creating the first edge in response to the analysis of the spatial relationship and an identification of a temporal overlap of pulse trains between the first stimulation block and the second stimulation block.

4. The system of claim 2, wherein constructing the graphical representation comprises:
creating the first edge in response to the analysis of the spatial relationship and an identification of a temporal overlap of pulse trains between the first stimulation block and the second stimulation block that exceeds a predetermined degree of freedom.

5. The system of claim 2, wherein analyzing the spatial relationship comprises:
calculating a spatial interference model of the first stimulation block and the second stimulation block.

6. The system of claim 5, wherein the spatial interference model is either a generic model or a patient-specific model.

7. The system of claim 1, wherein reconfiguring the at least one of the first stimulation block or the second stimulation block includes reconfiguring:
at least one of the first or second pulse train,
at least one of the first or the second electrode configuration, or
at least one of the first amplitude or the second amplitude.

8. The system of claim 7, wherein:
reconfiguring the at least one of the first stimulation block or the second stimulation block includes reconfiguring the at least one of the first amplitude or the second amplitude; and
reconfiguring the at least one of the first amplitude or the second amplitude includes, for each one of at least one of the first stimulation block or the second stimulation block, determining:
a difference between a maximum value of an activating function and a threshold to determine an amount of injected current needed to reach the threshold and trigger an action potential at a targeted fiber, and
wherein the activating function is based on a transfer function between a current stimulation of the one of the at least one of the first stimulation block or the second stimulation block and a second derivative of a potential field along the targeted fiber.

9. The system of claim 1, wherein identifying the first spatial section comprises identifying a cycle of the first node formed by a path of edges and nodes through which the first node is reachable.

10. A method for providing neurostimulation comprising:
obtaining a description of stimulation blocks, the stimulation blocks including:

a first stimulation block, the first stimulation block comprising a first electrode configuration, a first amplitude, and a first pulse train, and a second stimulation block, the second stimulation block comprising a second electrode configuration, a second amplitude, and a second pulse train;

constructing a graphical representation of interference relationships between the stimulation blocks, the graphical representation including:

nodes representing the stimulation blocks, a first node representing the first stimulation block and a second node representing the second stimulation block; and edges connecting the nodes, a first edge connecting the first node to the second node indicating interference between the first stimulation block and the second stimulation block;

identifying a first spatial section including the first node and the second node using the graphical representation; and in response to the identification of the first spatial section, reducing interference between stimulation blocks corresponding to the nodes in the first spatial section by reconfiguring at least one of the first stimulation block or the second stimulation block.

11. The method of claim 10, wherein constructing the graphical representation comprises:

analyzing a spatial relationship between the first stimulation block and the second stimulation block.

12. The method of claim 11, wherein constructing the graphical representation comprises:

creating the first edge in response to the analysis of the spatial relationship and an identification of a temporal overlap of pulse trains between the first stimulation block and the second stimulation block.

13. The method of claim 11, wherein constructing the graphical representation comprises:

creating the first edge in response to the analysis of the spatial relationship and an identification of a temporal overlap of pulse trains between the first stimulation block and the second stimulation block that exceeds a predetermined degree of freedom.

14. The method of claim 11, wherein analyzing the spatial relationship comprises:

calculating a spatial interference model of the first stimulation block and the second stimulation block.

15. The method of claim 14, wherein the spatial interference model is either a generic model or a patient-specific model.

16. The method of claim 14, wherein the spatial interference model is based on an R-matrix model, and the R-matrix model is based on a transfer function between a current injected at each electrode associated with the first and the second stimulation block and a corresponding voltage induced at a surface of each electrode.

17. The method of claim 16, wherein the R-matrix model estimates interference based on a voltage variation induced on an electrode greater than a threshold variation.

18. The method of claim 14, wherein the spatial interference model is based on distance rules, and the distance rules are based on a first separation of the first and the second stimulation block with respect to a first reference axis and a second separation of the first and the second stimulation block with respect to a second reference axis, the first separation less than a first distance threshold and the second separation less than a second distance threshold.

19. The method of claim 14, wherein the spatial interference model is based on a number of action potentials triggered at targeted neuron fibers.

20. The method of claim 14, wherein the spatial interference model is based on an activating function for each of the first and the second stimulation block, the activating function based on a transfer function between each current stimulation and a second derivative of a potential field along a targeted fiber.

21. The method of claim 10, wherein reconfiguring the at least one of the first stimulation block or the second stimulation block includes reconfiguring:

at least one of the first or second pulse train, at least one of the first or the second electrode configuration, or at least one of the first amplitude and the second amplitude.

22. The method of claim 10, wherein identifying the first spatial section comprises identifying a cycle of the first node formed by a path of edges and nodes through which the first node is reachable.

* * * * *